United States Patent
Yamato et al.

[11] Patent Number: 6,004,724
[45] Date of Patent: Dec. 21, 1999

[54] OXIME SULFONATES AND THE USE THEREOF AS LATENT SULFONIC ACIDS

[75] Inventors: Hitoshi Yamato, Hyogo; Hartmut Bleier; Jean-Luc Birbaum, both of Kobe, all of Japan; Martin Kunz, Efringen-Kirchen, Germany; Kurt Dietliker, Fribourg, Switzerland; Christoph De Leo, Ehrenkirchen, Germany; Toshikage Asakura, Minoo, Japan

[73] Assignee: Ciba Specialty Chemicals Corporation, Tarrytown, N.Y.

[21] Appl. No.: 09/104,676

[22] Filed: Jun. 25, 1998

[30] Foreign Application Priority Data

Jul. 1, 1997 [EP] European Pat. Off. ............ 97810422

[51] Int. Cl.⁶ ............... G03C 1/725; G03C 1/72; G07C 249/04; G07C 251/32
[52] U.S. Cl. ............... 430/281.1; 430/270.1; 430/913; 430/916; 430/919; 430/921; 564/253; 549/75; 549/68; 558/408; 546/294; 548/556
[58] Field of Search ............... 549/29, 75, 68; 564/253; 558/44, 408; 522/57; 430/270.1, 281.1, 916, 919, 921, 927, 924, 913, 300; 548/556; 546/294

[56] References Cited

U.S. PATENT DOCUMENTS 4,540,598 9/1985 Berner et al. ............ 427/54.1
4,736,055 4/1988 Dietliker et al. ............ 560/13

FOREIGN PATENT DOCUMENTS 0571330 11/1993 European Pat. Off. .
2306958 5/1997 United Kingdom .

OTHER PUBLICATIONS

Derwent Abstract 93–370703/47 for European Patent 0571330.

*Primary Examiner*—Janet Baxter
*Assistant Examiner*—Yvette M. Clarke
*Attorney, Agent, or Firm*—Luther A. R. Hall; David R. Crichton

[57] ABSTRACT

New oximsulfonate compounds of the formulae I or II,

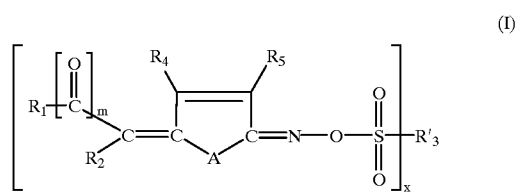

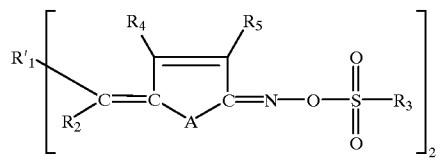

wherein m is 0 or 1; x is 1 or 2; $R_1$ is, for example phenyl, which is unsubstituted or substituted or $R_1$ is a heteroaryl radical that is unsubstituted or substituted, or, if m is 0, $R_1$ additionally is $C_2$–$C_6$alkoxycarbonyl, phenoxycarbonyl or CN; $R'_1$ is for example $C_2$–$C_{12}$alkylene, phenylene; $R_2$ has for example one of the meanings of $R_1$; n is 1 or 2; $R_3$ is for example $C_1$–$C_{18}$alkyl, $R'_3$ when x is 1, has one of the meanings given for $R_3$, or $R'_3$ in the formula IV and when x is 2 in the formula 1, is for example $C_2$–$C_{12}$alkylene, phenylene; $R_4$ and $R_5$ are independently of each other for example hydrogen, halogen, $C_1$–$C_6$alkyl; $R_6$ is for example hydrogen, phenyl; $R_7$ and $R_8$ are independently of each other for example hydrogen or $C_1$–$C_{12}$-alkyl; $R_9$ is for example $C_1$–$C_{12}$ alkyl; A is S, O, $NR_6$, or a group of formula A1, A2, A3 or A4

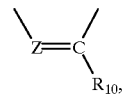

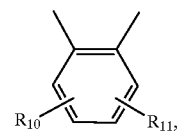

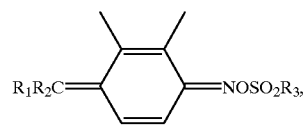

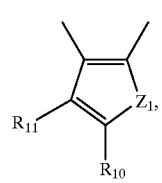

$R_{10}$ and $R_{11}$ independently of each other have one of the meanings given for $R_4$; $R_{12}$, $R_{13}$, $R_{14}$ and $R_{15}$ independently of one another are for example hydrogen, $C_1$–$C_4$alkyl; Z is $CR_{11}$ or N; $Z_1$ is —$CH_2$—, S, O or $NR_6$, are useful as latent sulfonic acids, especially in photoresist applications.

13 Claims, No Drawings

OXIME SULFONATES AND THE USE THEREOF AS LATENT SULFONIC ACIDS

The invention relates to new oximesulfonate compounds, photopolymerisable compositions comprising said compounds and to the use of the compounds as latent sulfonic acid photoinitiators, which can be activated by irradiation with light.

In U.S. Pat. No. 4,540,598 surface-coating compositions based on photosensitive oxime sulfonates and customary acid-curable resins are disclosed. In EP 571330 the use of α-(4-toluene-sulfonyloxyimino)-4-methoxybenzyl cyanide and α(4-toluene-sulfonyloxyimino)-3-thienylmethyl cyanide as latent acid donors in positive and negative photoresists for wavelengths of 340–390 nm, especially those in the radiation region of the mercury i line (365 nm) is described. In GB 2306958 the use of oxime-sulfonates as latent acid donors in positive and negative photoresists for wavelengths between 180 and 600 nm, especially those in the radiation region beyond 390 nm is reported.

In the art, a need still exists, especially for reactive non-ionic latent acid donors that are thermally and chemically stable and that, after being activated by light, can be used as catalysts for a variety of acid-catalysed reactions, such as polycondensation reactions, acid-catalysed depolymerisation reactions, acid-catalysed electrophilic substitution reactions or the acid-catalysed removal of protecting groups. There is also a need for compounds that when irradiated with light are converted into acids and are capable of acting as solubility inhibitors in resist formulations. Furthermore there is a need for photolatent acids which can be bleached upon irradiation.

Surprisingly, it has now been found that specific oxime-sulfonates are especially suitable as catalysts for such reactions. The optical absorption spectra of the specific compounds of the invention are particularly tunable over a wide range of the electromagnetic spectrum. Furthermore they can be bleached upon irradiation.

Such oximesulfonates are for example represented by the formulae I, II, III or IV

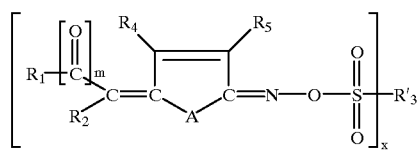

(I)

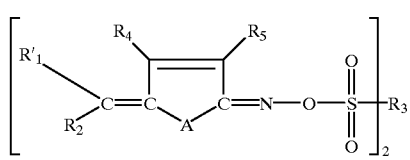

(II)

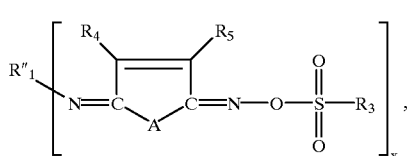

(III)

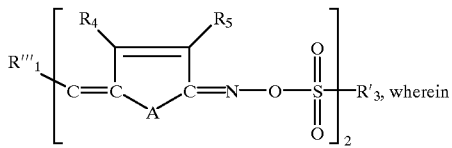

(IV)

m is 0 or 1; x is 1 or 2; $R_1$ is phenyl, which is unsubstituted or substituted by one or more of the radicals $C_1$–$C_{12}$alkyl, $C_1$–$C_4$haloalkyl, phenyl, $OR_6$, $NR_7R_8$, $SR_9$ and/or —S-phenyl, being possible for the substituents $OR_6$, $SR_9$ and $NR_7R_8$, to form 5- or 6-membered rings, via the radicals $R_6$, $R_7$, $R_8$ and/or $R_9$, with further substituents on the phenyl ring or with one of the carbon atoms of the phenyl ring, or $R_1$ is naphthyl, anthracyl or phenanthryl, the radicals naphthyl, anthracyl and phenanthryl being unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the naphthyl, anthracyl or phenanthryl ring or with one of the carbon atoms of the naphthyl, anthracyl or phenanthryl ring, or $R_1$ is a heteroaryl radical that is unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the heteroaryl ring or with one of the carbon atoms of the heteroaryl ring, or, if m is 0, $R_1$ additionally is $C_2$–$C_6$alkoxycarbonyl, phenoxycarbonyl or CN; or $R_1$ is H or $C_1$–$C_{12}$alkyl, with the proviso that $R_2$ is not simultaneously H or alkyl; $R'_1$ is $C_2$–$C_{12}$alkylene, phenylene, naphthylene,

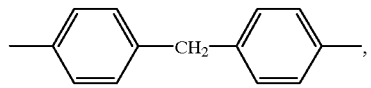

diphenylene or oxydiphenylene, these radicals being unsubstituted or substituted by $C_1$–$C_{12}$alkyl; $R''_1$ when x is 1, is phenyl which is unsubstituted or substituted by one or more of the radicals $C_1$–$C_{12}$alkyl, $C_1$–$C_4$-haloalkyl, phenyl, $OR_6$, $NR_7R_8$, $SR_9$, and/or —S-phenyl, it being possible for the substituents $OR_6$, $NR_7R_8$ and $SR_9$ to form 5- or 6-membered rings, via the radicals $R_6$, $R_7$, $R_8$ and/or $R_9$, with further substituents on the phenyl ring or with one of the carbon atoms of the phenyl ring, or $R''_1$ is naphthyl, anthracyl or phenanthryl, the radicals naphthyl, anthracyl and phenanthryl being unsubstituted or substituted by $C_1$–$C_6$alkyl, phenyl, $OR_6$, $NR_7R_8$, $SR_9$, and/or —S-phenyl, it being possible for the substituents $OR_6$, $NR_7R_8$ and $SR_9$ to form 5- or 6-membered rings, via the radicals $R_6$, $R_7$, $R_8$ and/or $R_9$, with further substituents on the naphthyl, anthracyl or phenanthryl ring, or with one of the carbon atoms of the naphthyl, anthracyl or phenanthryl ring, or $R''_1$ is a heteroaryl radical which is unsubstituted or substituted by $C_1$–$C_6$alkyl, phenyl, $OR_6$, $NR_7R_8$, $SR_9$ and/or —S-phenyl, it being possible for the substituents $OR_6$, $NR_7R_8$ and $SR_9$ to form 5- or 6-membered rings, via the radicals $R_6$, $R_7$, $R_8$ and/or $R_9$, with further substituents on the heteroaryl ring, or with one of the carbon atoms of the heteroaryl ring, or $R''_1$, when x=2, has one of the meanings of $R'_1$; $R'''_1$ is phenyl, which is unsubstituted or substituted by one or more of the radicals $C_1$–$C_{12}$alkyl, $C_1$–$C_4$haloalkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$, with further substituents on the phenyl ring or with one of the carbon atoms of the phenyl ring, or $R'''_1$ is naphthyl, anthracyl or phenanthryl, the radicals naphthyl, anthracyl and phenanthryl being unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and /or $R_9$ with further substituents on the naphthyl, anthracyl or phenanthryl ring or with one of the carbon atoms of the naphthyl, anthracyl or phenanthryl ring, or $R'''_1$ is a heteroaryl radical that is unsubstituted or substituted by $C_1$–$C_6$alkyl, phenyl, $OR_6$, $NR_7R_8$, $SR_9$ and/or —S-phenyl, it being possible for the substituents $OR_6$, $SR_9$ and $NR_7R_8$ to form 5- or 6-membered rings, via the radicals $R_6$, $R_7$, $R_8$ and/or $R_9$ with further substituents on the heteroaryl ring or with one of the carbon atoms of the heteroaryl ring; $R_2$ has one of the meanings of $R_1$ or is unsubstituted or CN-substituted phenyl, $C_2$–$C_6$alkanoyl, benzoyl that is unsubstituted or substituted by $C_1$–$C_6$alkyl, phenyl, $OR_6$, $SR_9$, $NR_7R_8$ and/or —S-phenyl, or $R_2$ is phenoxycarbonyl, $NO_2$, $C_1$–$C_4$haloalkyl, $S(O)_nC_1$–$C_6$alkyl, unsubstituted or $C_1$–$C_{12}$alkyl-substituted $S(O)_n$—$C_6$–$C_{12}$aryl, $SO_2O$—$C_1$–$C_6$alkyl, $SO_2O$—$C_6$aryl, diphenyl-phosphinoyl or $NHCONH_2$, or $R_1$ and $R_2$ together with the CO group, form a 5- or 6-membered ring that is unsubstituted or substituted by $C_1$–$C_6$alkyl, phenyl, $OR_6$, $SR_9$, $NR_7R_8$ and/or —S-phenyl, and said ring may additionally be interrupted by O, S, $NR_7$ and/or by CO, and to which ring one or more benzo radicals may be fused; n is 1 or 2; or $R_3$ is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or substituted by one or more of the radicals halogen, $C_1$–$C_4$haloalkyl, CN, $NO_2$, $C_1$–$C_{16}$alkyl, phenyl, $OR_6$, $COOR_9$, —OCO—$C_1$–$C_6$alkyl, $SO_2OR_9$ and/or $NR_7R_8$; $R'_3$ when x is 1, has one of the meanings given for $R_3$, or $R'_3$ in the formula IV and when x is 2 in the formula I, is $C_2$–$C_{12}$alkylene, phenylene, naphthylene,

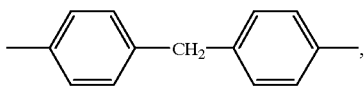

diphenylene or oxydiphenylene, these radicals being unsubstituted or substituted by $C_1$–$C_{12}$alkyl; $R_4$ and $R_5$ are independently of each other hydrogen, halogen, $C_1$–$C_6$alkyl, $C_1$–$C_6$alkoxy, $C_1$–$C_4$haloalkyl, CN, $NO_2$, $C_2$–$C_6$-alkanoyl, benzoyl, phenyl, —S-phenyl, $OR_6$, $SR_9$, $NR_7R_8$, $C_2$–$C_6$alkoxycarbonyl, phenoxycarbonyl, $S(O)_nC_1$–$C_6$alkyl, unsubstituted or $C_1$–$C_{12}$alkyl-substituted $S(O)_n$—$C_6$–$C_{12}$aryl, $SO_2O$—$C_1$–$C_6$alkyl, $SO_2O$—$C_6$–$C_{10}$aryl or $NHCONH_2$, or $R_4$ and $R_5$ together are —$C(R_{12})$=$C(R_{13})$—$C(R_{14})$=$C(R_{15})$—; $R_6$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl and said $C_1$–$C_{12}$alkyl may additionally be interrupted by —O—; $R_7$ and $R_8$ are independently of each other hydrogen or $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl and said $C_1$–$C_{12}$alkyl may additionally be interrupted by —O—, or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_7$ and $R_8$, together with the nitrogen atom to which they are bonded, form a 5-, 6- or 7-membered ring which may be interrupted by —O— or by —$NR_6$—; $R_9$ is $C_1$–$C_{12}$ alkyl which is unsubstituted or substituted by OH and/or $C_1$–$C_4$alkoxy and said $C_1$–$C_{12}$alkyl may additionally be interrupted by —O—; A is S, O, $NR_6$, or a group of formula A1, A2, A3 or A4

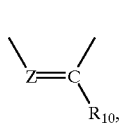

(A₁)

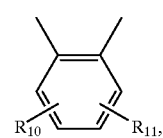

(A₂)

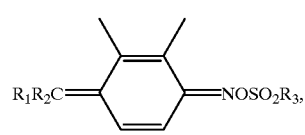

(A₃)

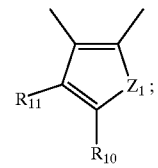

(A₄)

$R_{10}$ and $R_{11}$ independently of each other have one of the meanings given for $R_4$, or $R_{10}$ and $R_{11}$ together are —CO—$NR_6CO$—, or $R_{10}$ and $R_{11}$ together are —$C(R_{12})$=$C(R_{13})$—$C(R_{14})$=$C(R_{15})$—; $R_{12}$, $R_{13}$, $R_{14}$ and $R_{15}$ indepently of one another are hydrogen, $C_1$–$C_4$alkyl, halogen, phenyl, $OR_6$, $SR_9$, $NR_7R_8$, —S-phenyl, $C_2$–$C_6$alkoxycarbonyl, phenoxycarbonyl, CN, $NO_2$, $C_1$–$C_4$haloalkyl, $S(O)_nC_1$–$C_6$alkyl, unsubstituted or $C_1$–$C_{12}$alkyl-substituted $S(O)_n$—$C_6$–$C_{12}$aryl, $SO_2O$—$C_1$–$C_6$alkyl, $SO_2O$—$C_6$–$C_{10}$aryl or $NHCONH_2$; Z is $CR_{11}$ or N; $Z_1$ is —$CH_2$—, S, O or $NR_6$.

Accordingly, the present invention pertains to compounds of the formulae I or II

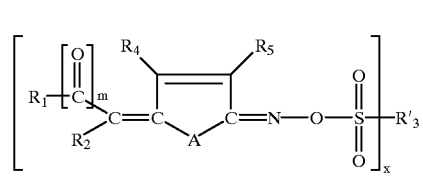

(I)

-continued

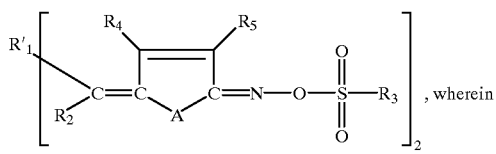, wherein m is 0 or 1;

x is 1 or 2;

R$_1$ is phenyl, which is unsubstituted or substituted by one or more of the radicals C$_1$–C$_{12}$alkyl, C$_1$–C$_4$haloalkyl, halogen, phenyl, OR$_6$, NR$_7$R$_8$, SR$_9$ and/or —S-phenyl, it being possible for the substituents OR$_6$, SR$_9$ and NR$_7$R$_8$ to form 5- or 6-membered rings, via the radicals R$_6$, R$_7$, R$_8$ and/or R$_9$, with further substituents on the phenyl ring or with one of the carbon atoms of the phenyl ring, or R$_1$ is naphthyl, anthracyl or phenanthryl, the radicals naphthyl, anthracyl and phenanthryl being unsubstituted or substituted by C$_1$–C$_6$alkyl, phenyl, OR$_6$, NR$_7$R$_8$, SR$_9$ and/or —S-phenyl, it being possible for the substituents OR$_6$, SR$_9$ and NR$_7$R$_8$ to form 5- or 6-membered rings, via the radicals R$_6$, R$_7$, R$_8$ and /or R$_9$ with further substituents on the naphthyl, anthracyl or phenanthryl ring or with one of the carbon atoms of the naphthyl, anthracyl or phenanthryl ring, or R$_1$ is a heteroaryl radical that is unsubstituted or substituted by C$_1$–C$_6$alkyl, phenyl, OR$_6$, NR$_7$R$_8$, SR$_9$ and/or —S-phenyl, it being possible for the substituents OR$_6$, SR$_9$ and NR$_7$R$_8$ to form 5- or 6-membered rings, via the radicals R$_6$, R$_7$, R$_8$ and/or R$_9$ with further substituents on the heteroaryl ring or with one of the carbon atoms of the heteroaryl ring, or, if m is 0, R$_1$ additionally is C$_2$–C$_6$alkoxycarbonyl, phenoxycarbonyl or CN; or R$_1$ is H or C$_1$–C$_{12}$alkyl, with the proviso that R$_2$ is not simultaneously H or alkyl;

R'$_1$ is C$_2$–C$_{12}$alkylene, phenylene, naphthylene,

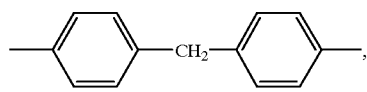

diphenylene or oxydiphenylene, the radicals phenylene, naphthylene,

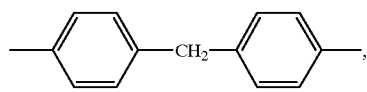

diphenylene and oxydiphenylene being unsubstituted or substituted by C$_1$–C$_{12}$alkyl;

R$_2$ has one of the meanings of R$_1$ or is unsubstituted or CN-substituted phenyl, C$_2$–C$_6$-alkanoyl, benzoyl that is unsubstituted or substituted by C$_1$–C$_6$alkyl, phenyl, OR$_6$, SR$_9$, NR$_7$R$_8$ and/or —S-phenyl, or R$_2$ is phenoxycarbonyl, NO$_2$, C$_1$–C$_4$haloalkyl, S(O)$_n$C$_1$–C$_6$alkyl, unsubstituted or C$_1$–C$_{12}$alkyl-substituted S(O)$_n$—C$_6$–C$_{12}$aryl, SO$_2$O—C$_1$–C$_6$alkyl, SO$_2$O—C$_6$–C$_{10}$aryl, diphenyl-phosphinoyl or NHCONH$_2$, or R$_1$ and R$_2$ together with the CO group, form a 5- or 6-membered ring that is unsubstituted or substituted by C$_1$–C$_6$alkyl, phenyl, OR$_6$, SR$_9$, NR$_7$R$_8$ and/or —S-phenyl, and said ring may additionally be interrupted by O, S, NR$_7$ and/or by CO, and to which ring one or more benzo radicals may be fused;

n is 1 or 2; or

R$_3$ is C$_1$–C$_{18}$alkyl, phenyl-C$_1$–C$_3$alkyl, camphoryl, C$_1$–C$_{10}$haloalkyl, phenyl, naphthyl, anthracyl or phenanthryl, the radicals phenyl, naphthyl, anthracyl and phenanthryl being unsubstituted or substituted by one or more of the radicals halogen, C$_1$–C$_4$haloalkyl, CN, NO$_2$, C$_1$–C$_{16}$alkyl, phenyl, OR$_6$, COOR$_9$, —OCO—C$_1$–C$_4$alkyl, SO$_2$OR$_9$ and/or NR$_7$R$_8$;

R'$_3$ when x is 1, has one of the meanings given for R$_3$, and when x is 2, R'$_3$ is C$_2$–C$_{12}$alkylene, phenylene, naphthylene,

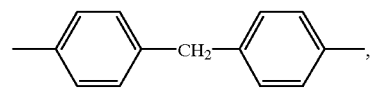

diphenylene or oxydiphenylene, the radicals phenylene, naphthylene,

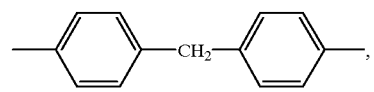

diphenylene and oxydiphenylene being unsubstituted or substituted by C$_1$–C$_{12}$alkyl;

R$_4$ and R$_5$ are independently of each other hydrogen, halogen, C$_1$–C$_6$alkyl, C$_1$–C$_6$alkoxy, C$_1$–C$_4$haloalkyl, CN, NO$_2$, C$_2$–C$_6$alkanoyl, benzoyl, phenyl, —S-phenyl, OR$_6$, SR$_9$, NR$_7$R$_8$, C$_2$–C$_6$alkoxycarbonyl, phenoxycarbonyl, S(O)$_n$C$_1$–C$_6$alkyl, unsubstituted or C$_1$–C$_{12}$alkyl-substituted S(O)$_n$—C$_6$–C$_{12}$aryl, SO$_2$O—C$_1$–C$_6$alkyl, SO$_2$O—C$_6$–C$_{10}$aryl or NHCONH$_2$, or R$_4$ and R$_5$ together are —C(R$_{12}$)=C(R$_{13}$)—C(R$_{14}$)=C(R$_{15}$)—;

R$_6$ is hydrogen, phenyl, C$_1$–C$_{12}$alkyl which is unsubstituted or substituted by phenyl, OH, C$_1$–C$_{12}$alkoxy, C$_1$–C$_{12}$alkylsulfonyl, phenylsulfonyl, (4-methylphenyl)sulfonyl and/or by C$_2$–C$_6$alkanoyl and said C$_1$–C$_{12}$alkyl may additionally be interrupted by —O—;

R$_7$ and R$_8$ are independently of each other hydrogen or C$_1$–C$_{12}$alkyl which is unsubstituted or substituted by OH, C$_1$–C$_4$alkoxy, C$_1$–C$_{12}$alkylsulfonyl, phenylsulfonyl, (4-methylphenyl)sulfonyl and/or C$_1$–C$_6$alkanoyl and said C$_1$–C$_{12}$alkyl may additionally be interrupted by —O—, or R$_7$ and R$_8$ are phenyl, C$_2$–C$_6$alkanoyl, benzoyl, C$_1$–C$_6$alkylsulfonyl, phenylsulfonyl, (4-methyphenyl)sulfonyl, naphthysulfonyl, anthracylsulfonyl or phenanthrylsulfonyl, or R$_7$ and R$_8$, together with the nitrogen atom to which they are bonded, form a 5-, 6- or 7-membered ring which may be interrupted by —O—or by —NR$_6$—;

R$_9$ is C$_1$–C$_{12}$ alkyl which is unsubstituted or substituted by OH and/or C$_1$–C$_4$alkoxy and said C$_1$–C$_{12}$alkyl may additionally be interrupted by —O—;

A is S, O, NR$_6$, or a group of formula A1, A2, A3 or A4

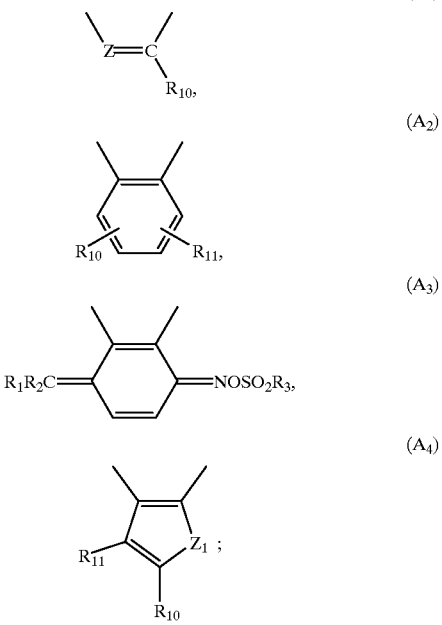

R$_{10}$ and R$_{11}$ independently of each other have one of the meanings given for R$_4$, or R$_{10}$ and R$_{11}$ together are —CO—NR$_6$CO—, or R$_{10}$ and R$_{11}$ together are —C(R$_{12}$)═C(R$_{13}$)—C(R$_{14}$)═C(R$_{15}$)—;

R$_{12}$, R$_{13}$, R$_{14}$ and R$_{15}$ independently of one another are hydrogen, C$_1$–C$_4$alkyl, halogen, phenyl, OR$_6$, SR$_9$, NR$_7$R$_8$, —S-phenyl, C$_2$–C$_6$alkoxycarbonyl, phenoxycarbonyl, CN, NO$_2$, C$_1$–C$_4$haloalkyl, S(O)$_n$C$_1$–C$_6$alkyl, unsubstituted or C$_1$–C$_{12}$alkyl-substituted S(O)$_n$—C$_6$–C$_{12}$aryl, SO$_2$O—C$_1$–C$_6$alkyl, SO$_2$O—C$_6$–C$_{10}$aryl or NHCONH$_2$;

Z is CR$_{11}$ or N;

Z$_1$ is —CH$_2$—, S, O or NR$_6$.

C$_1$–C$_{18}$Alkyl is linear or branched and is, for example, C$_1$–C$_{12}$-, C$_1$–C$_8$-, C$_1$–C$_6$- or C$_1$–C$_4$-alkyl Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl. For example, R$_3$ is C$_1$–C$_8$alkyl, especially C$_1$–C$_6$alkyl, preferably C$_1$–C$_4$alkyl, such as methyl, isopropyl or butyl.

C$_1$–C$_{16}$Alkyl and C$_1$–C$_{12}$alkyl are likewise linear or branched and are, for example, as defined above up to the appropriate number of carbon atoms. Of interest are, for example, C$_1$–C$_8$-, especially C$_1$–C$_6$-, preferably C$_1$–C$_4$- alkyl, such as methyl or butyl.

C$_2$–C$_{12}$Alkyl, which is interrupted once or several times by —O— or by —S—, is interrupted, for example, from one to five times, for example from one to three times or once or twice, by —O—or —S—. That results in structural units such as: —S(CH$_2$)$_2$OH, —O(CH$_2$)$_2$OH, —O(CH$_2$)$_2$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]$_y$—CH$_3$, wherein y=1–5, —(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$CH$_3$.

C$_5$–C$_{12}$Cycloalkyl is, for example, cyclopentyl, cyclohexyl, cyclooctyl, cyclododecyl, especially cyclopentyl and cyclohexyl, preferably cyclohexyl.

C$_2$–C$_{12}$Alkylene is linear or branched and is, for example, C$_2$–C$_8$-, C$_2$–C$_6$- or C$_2$–C$_4$-alkylene. Examples are ethylene, propylene, butylene, pentylene, hexylene, heptylene, octylene, nonylene, decylene, undecylene and dodecylene. For example, R$_3$ is C$_1$–C$_8$alkylene, especially C$_1$–C$_6$alkylene, preferably C$_1$–C$_4$alkylene, such as methylene or butylene.

Substituted phenyl carries from one to five, for example one, two or three, especially one or two, substituents on the phenyl ring. The substitution is preferably in the 4-, 3,4-, 3,5- or 3,4,5-position of the phenyl ring. When the radicals naphthyl, phenanthryl, heteroaryl and anthracyl are substituted by one or more radicals, they are, for example, mono- to penta-substituted, for example mono-, di- or tri-substituted, especially mono- or di-substituted.

When R$_1$ is a phenyl radical substituted by OR$_6$, NR$_7$R$_8$ and/or by SR$_9$ and the substituents OR$_6$, NR$_7$R$_8$ and SR$_9$ form 5- or 6-membered rings, via the radicals R$_6$, R$_7$, R$_8$ or R$_9$, with other substituents on the phenyl ring or with one of the carbon atoms of the phenyl ring, for example the following structural units are obtained

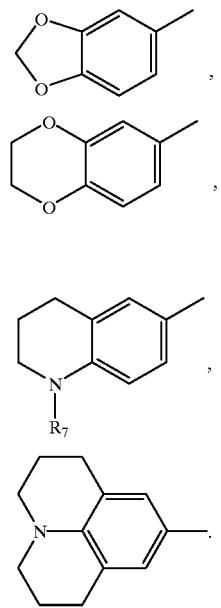

In the present application, the term "heteroaryl" denotes unsubstituted and substituted radicals, for example 2-thienyl,

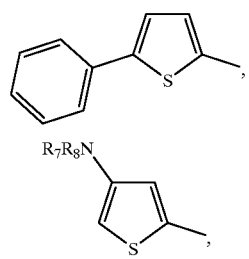

wherein R$_7$ and R$_8$ are as defined above, thianthrenyl, isobenzofuranyl, xanthenyl, phenoxanthiinyl,

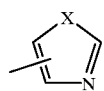

or

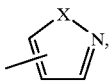

wherein X is S, O or NR$_7$ and R$_7$ is as defined above. Examples thereof are pyrazolyl, thiazolyl, oxazolyl, isothiazolyl or isoxazolyl. Also included are, for example, furyl, pyrrolyl, 1,2,4-triazolyl,

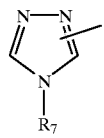

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

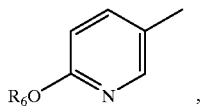

wherein R$_6$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

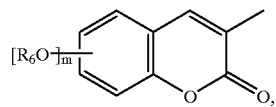

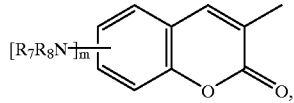

wherein R$_6$, R$_7$, R$_8$ and m are as defined above,

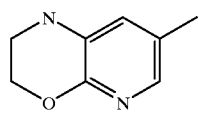

or anthraquinonyl. Each of the heteroaryls may carry the substituents indicated above or in claim 1.

Camphoryl is

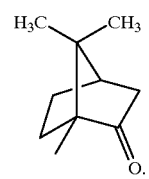

When R$_1$ and R$_2$ together with the CO group form a 5- or 6-membered ring, it is, for example, a cyclopentane, cyclohexane, pyran or piperidine ring. There may be fused to that ring, for example, also benzo, naphtho, anthraceno, phenanthreno or heteroaryl radicals, there being formed structures such as

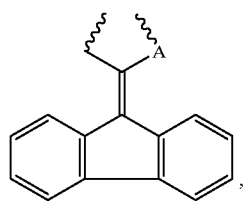

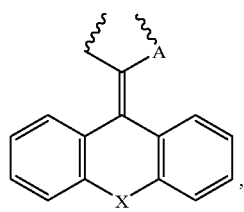

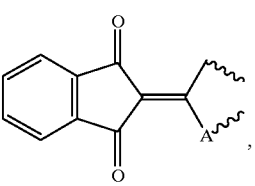

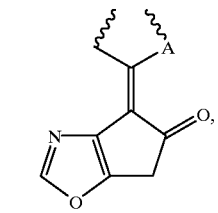

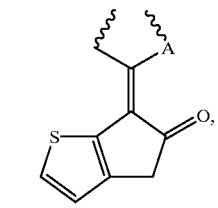

-continued

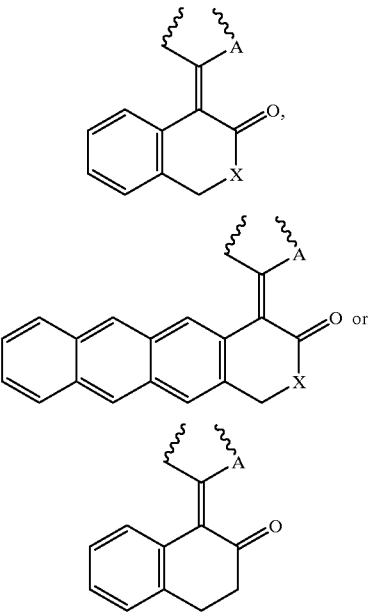

wherein "〰️" denote the remaining parts of formula I, and wherein X is S, O or NR₇ and R₇ is as defined above, and in which structures the aromatic rings may carry further substituents as definded above and in claim 1.

Apparently these structures are not strictly "R₁ and R₂ together", but are partial illustrations of the final compounds. They are, for example, also tetrahydronaphthalene, dihydroanthracene, indan, chroman, fluorene, xanthene or thioxanthene ring systems. When the ring contains carbonyl groups, for example benzoquinone, naphthoquinone or anthraquinone radicals are formed.

$C_1$–$C_6$Alkanoyl is, for example, formyl, acetyl, propionyl, butanoyl or hexanoyl, especially acetyl.

$C_1$–$C_4$Alkoxy is, for example, methoxy, ethoxy, propoxy and butoxy, it being possible for the alkyl radicals in alkoxy groups having more than two carbon atoms also to be branched.

$C_2$–$C_6$Alkoxycarbonyl is ($C_1$–$C_5$alkyl)-O—C(O)—, wherein $C_1$–$C_5$alkyl is as defined above up to the appropriate number of carbon atoms. Examples are methoxycarbonyl, ethoxycarbonyl, propoxycarbonyl, butoxycarbonyl or pentyloxycarbonyl, it being possible for the alkyl radicals in alkoxy groups having more than two carbon atoms also to be branched.

$C_1$–$C_{10}$Haloalkyl and $C_{1-C4}$haloalkyl are $C_1$–$C_{10}$- and $C_1$–$C_4$-alkyl mono- or poly-substituted by halogen, $C_1$–$C_{10}$- and $C_1$–$C_4$-alkyl being, for example, as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl.

Halogen is fluorine, chlorine, bromine or iodine, especially chlorine or fluorine, preferably chlorine.

In a group S(O)$_n$—$C_6$–$C_{10}$aryl that may be unsubstituted or substituted by $C_1$–$C_{12}$alkyl, the aryl radical is phenyl, tosyl, dodecylphenylsulfonyl or 1- or 2-naphthyl.

Phenyl-$C_1$–$C_3$alkyl is, for example, benzyl, 2-phenylethyl, 3-phenylpropyl, α-methylbenzyl or α,α-dimethylbenzyl, especially benzyl.

Oxydiphenylene is

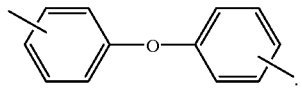

When R₇ and R₈ together with the nitrogen atom to which they are bonded form a 5-, 6- or 7-membered ring that may be interrupted by —O— or by —NR₆—, for example the following structures are obtained

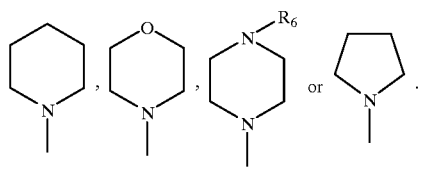

Preference is given to compounds of formula I and II, wherein m is 0; x is 1; R₁ is unsubstituted phenyl or phenyl which is substituted by $C_1$–$C_6$alkyl, phenyl, OR₆, SR₉, —S-phenyl, halogen and/or by NR₇R₆, it being possible for the substituents OR₆, and NR₇R₈ to form 5- or 6-membered rings, via the radicals R₆, R₇ and/or R₈ with further substituents of the phenyl ring, or with one of the carbon atoms of the phenyl ring; R'₁ is phenylene, naphthylene,

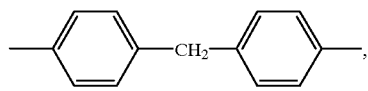

diphenylene or oxydiphenylene, the radicals phenylene, naphthylene,

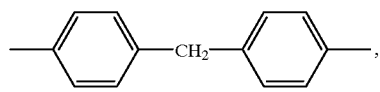

diphenylene and oxydiphenylene being unsubstituted or substituted by $C_1$–$C_{12}$alkyl.

Other interesting compounds are those of formula I, wherein x is 1; m is 0; R₁ is unsubstituted phenyl or phenyl substituted once or twice by $C_1$–$C_4$alkyl, $C_1$–$C_4$alkoxy or halogen; R₂ is CN; R₃ is $C_1$–$C_{16}$alkyl or unsubstituted or $C_1$–$C_4$alkyl-substituted phenyl; R₄ and R₅ independently of each other are hydrogen, $C_1$–$C_4$alkyl or $C_1$–$C_4$alkoxy; A is —S— or a group of the formula A₁; Z is CR₁₁; and R₁₀ and R₁₁ are hydrogen.

Compounds of the formula I, wherein m is 0 and x is 1 are specifically preferred and in the following are referred to as compounds of the formula Ia

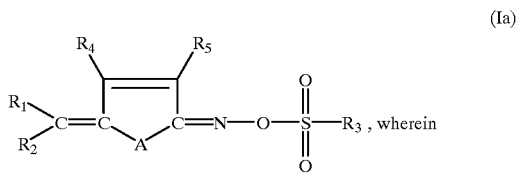

(Ia)

R₁, R₂, R₃, R₄, R₅ and A are as defined above.

Preferred are compounds of formula Ia, wherein R₁ is unsubstituted phenyl or phenyl substituted once or twice by $C_1$–$C_4$alkyl, $OR_6$ or halogen or $R_1$ is naphthyl or thienyl; $R_2$ is CN; $R'_3$ has one of the meanings of $R_3$ and is $C_1$–$C_{16}$alkyl, camphoryl or unsubstituted phenyl or phenyl substituted 1–5 times by $C_1$–$C_{12}$alkyl, $C_1$–$C_4$alkoxy, $C_1$–$C_4$haloalkyl, $C_1$–$C_4$alkylthio, $NO_2$ or halogen; $R_4$ and $R_5$ independently of each other are hydrogen, $C_1$–$C_4$alkyl, $C_1$–$C_4$alkoxy, $NR_7R_8$ or phenyl or $R_4$ and $R_5$ together are —C($R_{12}$)=C($R_{13}$)—C($R_{14}$)=C($R_{15}$)—; $R_6$ is $C_1$–$C_4$alkyl or $C_1$–$C_4$alkylsulfonyl; $R_7$ and $R_8$ independently of one another are hydrogen or phenyl; A is —S—, $NR_6$ or a group of the formula $A_1$

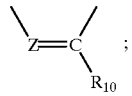

Z is $CR_{11}$ or N; and $R_{10}$, $R_{11}$, $R_{12}$, $R_{13}$, $R_{14}$ and $R_{15}$ are hydrogen.

Further compounds of interest are those wherein in the formula Ia, wherein $R_1$ is a heteroaryl radical that is unsubstituted or mono- or poly-substituted by $C_1$–$C_6$alkyl, phenyl, $OR_6$, $SR_9$, —S-phenyl and/or by $NR_7R_8$, it being possible for the substituents $OR_6$ and $NR_7R_8$ to form 5- or 6-membered rings, via the radicals $R_6$, $R_7$ and/or $R_8$, with further substituents or with one of the carbon atoms of the heteroaryl ring.

Further compounds of interest are those of the formula II, wherein $R'_1$ is phenylene, naphthylene,

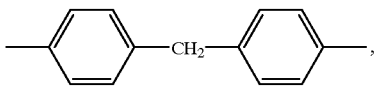

diphenylene or oxydiphenylene, the radicals phenylene, naphthylene,

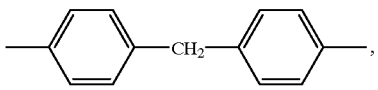

diphenylene and oxydiphenylene being unsubstituted or substituted by $C_1$–$C_{12}$alkyl;

Mention should be made of compounds of formula Ia and II wherein $R_2$ is CN, $C_2$–$C_6$alkoxycarbonyl, $C_1$–$C_4$haloalkyl, $S(O)_nC_1$–$C_6$alkyl, or unsubstituted or $C_1$–$C_{12}$alkyl-substituted $S(O)_n$—$C_6$–$C_{10}$aryl.

Other examples of compounds are those of formula Ia or II wherein $R_1$ and $R_2$ are CN, $C_2$–$C_6$alkoxycarbonyl, $C_1$–$C_4$haloalkyl, $S(O)_nC_1$–$C_6$alkyl, or unsubstituted or $C_1$–$C_{12}$alkyl-substituted $S(O)_n$—$C_6$–$C_{10}$aryl.

Most preferred compounds are those of formula Ia or II, where $R_1$ is phenyl (substituted as defined above) or a heteroaryl radical (substituted as defined above) and $R_2$ is CN.

Preference is given especially to compounds of formula Ia and II wherein $R_6$ is $C_1$–$C_6$alkyl that is unsubstituted or substituted by OH, $C_1$–$C_4$alkoxy, $C_1$–$C_{12}$alkylsulfonyl, phenylsulfonyl, (4-methylphenyl)sulfonyl and/or by $C_2$–$C_6$alkanoyl and that may additionally be interrupted by —O—.

Preference is given also to compounds of formula Ia and II wherein $R_3$ is $C_1$–$C_{18}$alkyl, $C_1$–$C_{10}$haloalkyl, or phenyl that is unsubstituted or substituted by halogen, $NO_2$, $C_1$–$C_4$haloalkyl, $C_1$–$C_{16}$alkyl or $C_1$–$C_{12}$alkyl, $OR_4$, $COOR_7$ and/or by —OCO—$C_1$–$C_4$alkyl Preference is given likewise compounds of formula Ia and II wherein $R_4$ and $R_5$ are independently of each other hydrogen, halogen, $C_1$–$C_6$ alkyl, $C_1$–$C_6$ alkoxy, $C_1$–$C_4$haloalkyl, $NO_2$, $C_2$–$C_6$alkanoyl, benzoyl, $OR_6$, or $R_4$ and $R_5$ together are —CH=CH—CH=CH—; $R_7$ and $R_8$ are independently of each other hydrogen or $C_1$–$C_{12}$alkyl that is unsubstituted or substituted by OH, $C_1$–$C_4$alkoxy, $C_1$–$C_{12}$alkylsuffonyl, phenylsulfonyl, (4-methylphenyl)sulfonyl and/or by $C_1$–$C_6$alkanoyl and that may additionally be interrupted by —O—, or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_7$ and $R_8$, together with the nitrogen atom to which they are bonded, form a 5-, 6- or 7-membered ring which may be interrupted by —O— or by —$NR_6$—; and $R_9$ is $C_1$–$C_{12}$ alkyl that is unsubstituted or substituted by OH and/or by $C_1$–$C_4$alkoxy and that may additionally be interrupted by —O—. A is S, O, $NR_6$, or a group of formula A1, A2 or A3; $R_{10}$ and $R_{11}$ independently of each other have one of the meanings of $R_4$; and Z is $CR_{11}$ or N.

Specific examples of compounds according to the present invention are (4-Methylsulfonyloxyimino-cyclohexa-2,5-dienylidene)-phenyl-acetonitrile;

(4-Methylsulfonyloxyimino-cyclohexa-2,5-dienylidene)-(4-methoxyphenyl)-acetonitrile;

(4-(4-Methylphenylsulfonyloxyimino)-cyclohexa-2,5-dienylidene)-(4-methoxyphenyl)-acetonitrile;

(4-Methylsulfonyloxyimino-cyclohexa-2,5-dienylidene)-(4-methylphenyl)-acetonitrile;

(4-Methylsulfonyloxyimino-cyclohexa-2,5-dienylidene)-(3-methylphenyl)-acetonitrile;

(4-Methylsulfonyloxyimino-cyclohexa-2,5-dienylidene)-(3,4-dimethylphenyl)-acetonitrile;

(4-Methylsulfonyloxyimino-cyclohexa-2,5-dienylidene)-thiophen-2-yl-acetonitrile;

(5-Methylsulfonyloxyimino-5H-thiophen-2-ylidene)-phenyl-acetonitrile;

(4-Methylsulfonyloxyimino-3-methylcyclohexa-2,5-dienylidene)-phenyl-acetonitrile;

(4-Methylsulfonyloxyimino-3-methoxycyclohexa-2,5-dienylidene)-phenyl-acetonitrile;

(4-Methylsulfonyloxyimino-cyclohexa-2,5-dienylidene)-(2-methylphenyl)-acetonitrile;

Biphenyl-4-yl-(4-methylsulfonyloxyimino-cyclohexa-2,5-dienylidene)-acetonitrile;

(4-Methylsulfonyloxyimino-cyclohexa-2,5-dienylidene)-(3,4-dimethoxyphenyl)-acetonitrile;

(4-Methylsulfonyloxyimino-2,5-dichlorocyclohexa-2,5-dienylidene)-phenyl-acetonitrile;

(4-Methylsulfonyloxyimino-cyclohexa-2,5-dienylidene)-(3-methoxyphenyl)-acetonitrile;

(5-Methylsultonyloxyimino-5H-thiophen-2-ylidene)-(4-methylphenyl)-acetonitrile;

(4-Methylsulfonyloxyimino-cyclohexa-2,5-dienylidene)-(4-chlorophenyl)-acetonitrile;

(4-Methylsulfonyloxyimino-cyclohexa-2,5-dienylidene)-naphthalen-1-yl-acetonitrile;

(5-Methylsulfonyloxyimino-5H-thiophen-2-ylidene)-(2-methylphenyl)-acetonitrile;

(4-Methylsulfonyloxyimino-cyclohexa-2,5-dienylidene)-(2-methoxyphenyl)-acetonitrile;

(5-Methylsulfonyloxyimino-5H-thiophen-2-ylidene)-(2,6-dichlorophenyl)-acetonitrile;

(4-(3-Nitro-5-trifluoromethylphenylsulfonyloxyimino)-cyclohexa-2,5-dienylidene)-phenyl-acetonitrile;

(4-Pentafluorophenylsulfonyloxyimino-cyclohexa-2,5-dienylidene)-phenyl-acetonitrile;
(5-Ethylsulfonyloxyimino-5H-thiophen-2-ylidene)-phenyl-acetonitrile;
(4-Methylsulfonyloxyimino-cyclohexa-2,5-dienylidene)-(2-chlorophenyl)-acetonitrile;
(5-Butylsulfonyloxyimino-5H-thiophen-2-ylidene)-phenyl-acetonitrile;
(5-Methylsulfonyloxyimino-6-methoxy-5H-pyridin-2-ylidene)-phenyl-acetonitrile;
(4-Methylsulfonyloxyimino-3-phenylcyclohexa-2,5-dienylidene)-phenyl-acetonitrile;
(5-Methylsulfonyloxyimino-5H-thiophen-2-ylidene)-(2-chlorophenyl)-acetonitrile;
(5-(3-Nitro-5-trifluoromethylphenylsulfonyloxyimino)-5H-thiophen-2-ylidene)-phenyl-acetonitrile;
(4-Butyl-5-methylsulfonyloxyimino -5H-thiophen-2-ylidene)-phenyl-acetonitrile;
(4-Methylsulfonyloxyimino-4H-naphthalen-1-ylidene)-(4-chlorophenyl)-acetonitrile;
(5-Pentafluorophenylsulfonyloxyimino-5H-thiophen-2-ylidene)-phenyl-acetonitrile;
(5-Methylsulfonyloxyimino-5H-thiophen-2-ylidene)-(4-methylsulfonyloxyphenyl)-acetonitrile;
(5-Methylsulfonyloxyimino-5H-thiophen-2-ylidene)-(2-methoxyphenyl)-acetonitrile;
(5-Methylsulfonyloxyimino-1-methyl-1,5-dihydro-pyrrol-2-ylidene)-phenyl-acetonitrile;
(4-Methylsulfonyloxyimino-3-phenylamino-cyclohexa-2,5-dienylidene)-phenyl-acetonitrile;
(5-(4-Methylphenylsulfonyloxyimino)-5H-thiophen-2-ylidene)-(2-methylphenyl)-acetonitrile;
(5-Butylsulfonyloxyimino-5H-thiophen-2-ylidene)-(2-methylphenyl)-acetonitrile;
(5-Hexadecylsulfonyloxyimino-5H-thiophen-2-ylidene)-(2-methylphenyl)-acetonitrile;
(5-Octylsulfonyloxyimino-5H-thiophen-2-ylidene)-(2-methylphenyl)-acetonitrile;
(4-Methylsulfonyloxyimino-cyclohexa-2,5-dienylidene)-(2,4-dichlorophenyl)-acetonitrile;
(4-Isopropylsulfonyloxyimino-cyclohexa-2,5-dienylidene)-(2,4-dichlorophenyl)-acetonitrile;
(4-Butylsulfonyloxyimino-cyclohexa-2,5-dienylidene)-(2,4-dichlorophenyl)-acetonitrile;
(4-Octylsulfonyloxyimino-cyclohexa-2,5-dienylidene)-(2,4-dichlorophenyl)-acetonitrile;
(4-(4-Methylphenyl)sulfonyloxyimino-cyclohexa-2,5-dienylidene)-(2,4-dichlorophenyl)-acetonitrile;
(4-(4-Dodecylphenyl)sulfonyloxyimino-cyclohexa-2,5-dienylidene)-(2,4-dichlorophenyl)-acetonitrile;
(4-(4-Dodecylphenyl)sulfonyloxyimino-cyclohexa-2,5-dienylidene)-phenyl-acetonitrile;
(5-(2,4,6-Trimethylphenylsulfonyloxyimino-5H-thiophen-2-ylidene)-(2-methylphenyl)-acetonitrile;
(4-Methylsulfonyloxyimino-cyclohexa-2,5-dienylidene)-(4-methylthiophenyl)-acetonitrile;
(5-(10-Camphorsulfonyloxyimino)-5H-thiophen-2-ylidene)-(2-methylphenyl)-acetonitrile;
(4-Methylsulfonyloxyimino-cyclohexa-2,5-dienylidene)-(4-(2-propylthio)phenyl)-acetonitrile;
(4-Methylsulfonyloxyimino-cyclohexa-2,5-dienylidene)-(3,4-dimethylthiophenyl)-acetonitrile;
(4-Methylsulfonyloxyimino-cyclohexa-2,5-dienylidene)-(4-dimethylaminophenyl)-acetonitrile;
(5-Methylsulfonyloxyimino-5H-thiophen-2-ylidene)-(4-(2-propyl)phenyl)-acetonitrile;
(5-Methylsulfonyloxyimino-5H-thiophen-2-ylidene)-(2-methylthiophenyl)-acetonitrile;
(5-Methylsulfonyloxyimino-5H-thiophen-2-ylidene)-(4-methylthiophenyl)-acetonitrile;
(5-Methylsulfonyloxyimino-5H-thiophen-2-ylidene)-(3,4-dimethoxyphenyl)-acetonitrile;
(5-Methylsulfonyloxyimino-5H-thiophen-2-ylidene)-(4-dimethylaminophenyl)-acetonitrile;
(5-Methylsulfonyloxyimino-5H-thiophen-2-ylidene)-thiophen-2-yl-acetonitrile.

The invention also relates to mixtures of isomeric forms of the compounds of formula I, Ia and II. Oximesulfonates can be present both in the syn (cis, Z) and the anti (trans, E) form or as mixtures of the two geometrical isomers. In addition, the substituted methylidene group $C(R_1)R_2$ can exhibit two (cis and trans) isomers. Depending on $R_4$, $R_5$ and A, this can result in up to for geometrical isomers. In the present invention, both the individual geometrical isomers and any mixtures of two, three or four geometrical isomers can be used.

Oximesulfonates (of formulae I, Ia and II) can be prepared by methods described in the literature, for example by reacting suitable free oximes (of formula IVa and IVb) with sulfonic acid halides (of formula V):

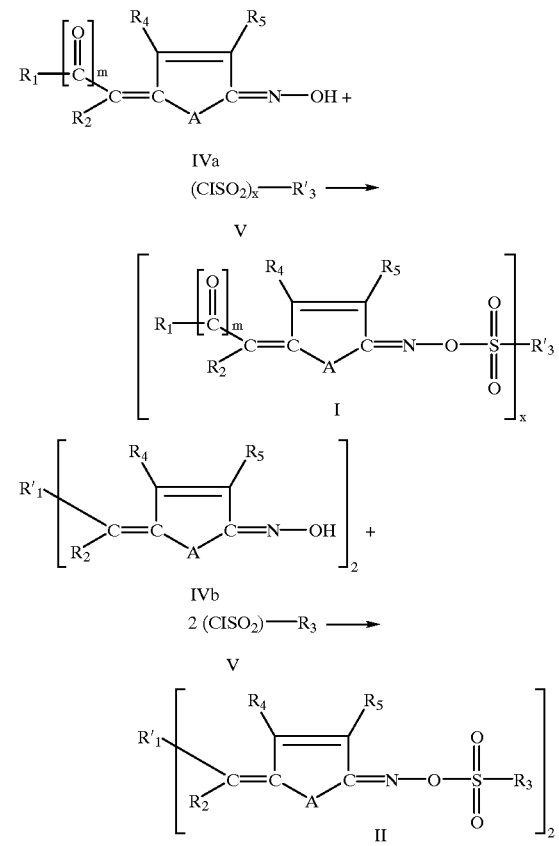

$R_1$, $R'_1$, $R_2$, $R_3$, $R_4$, $R_5$, A, m and x are as defined above.

These reactions are carried out in an inert solvent such as tetrahydrofuran (THF) or dimethylformamide (DMF) in the presence of a base, for example a tertiary amine, such as triethylamine, or by reaction of the salt of an oxime with a sulfonic acid chloride. Those methods are disclosed, for example, in EP-A 48615. The sodium salts of oximes can be obtained, for example, by reacting the oxime in question with a sodium alcoholate in DMF.

The oximes of formula IVa required for the reaction can be prepared according to known procedures, for example by reacting benzyl cyanides or cyanomethyl heterocycles with nitrobenzenes or nitronaphtalenes in the presence of a base (such as, for example, sodium methoxide or potassium hydroxide) in a polar solvent such as, for example, methanol or DMF, as described by R. B. Davis, L. C. Pizzini & E. J. Bara, *J. Org. Chem.* 26, 4270 (1961) or P. Fournary and T. Marey, *Bull. Soc. Chim. Fr.* 3223 (1968). Temperatures of −80° C. to 80° C., especially −10° C. to 60° C. are suitable for the reaction. Phase transfer catalysis is also suitable to prepare oxime intermediates of formula IVa. K. Takahashi, et al. have described the use of benzyltriethyl ammonium chloride and 50% aqueous sodium hydroxide for the reaction of nitrobenzene with benzyl cyanide (K. Takahashi, T. Tsuboi, K. Yamada, H. Iida, *Nippon Kagaku Kaishi* 144–7 (1976); Chemical Abstract No. 84:105162). Oximes of formula IVa and IVb have also been prepared as intermediates in the synthesis of various pharmaceutical compounds (e.g. U.S. Pat. Nos. 5,043,327, 5,521,187; EP-A-371564, EP-A-541153, ES-A-524551) or for use as UV absorbers (for instance, in U.S. Pat. No. 3,374,248).

Oximes can also be obtained by reacting a suitable carbonyl or thionylcarbonyl compound with hydroxylamine or a hydroxylammonium salt.

The preparation of sulfonic acid halides (of formula V), for example by halosulfonation or by the Reed reaction, is familiar to a person skilled in the art and is described, for example, in customary chemistry textbooks.

The invention relates also to the use of compounds of formulae I and II as descriibed above, as photoinitiators for compounds that can be crosslinked under the action of an acid and/or as solubility inhibitors for compounds the solubility of which is altered under the action of an acid.

In photocrosslinkable compositions, oximesulfonates act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Finally, oximesulfonates that are sparingly soluble in an aqueous-alkaline developer can be rendered soluble in the developer by means of light-induced conversion into the free acid, with the result that they can be used as solubility inhibitors in combination with suitable film-forming resins.

The invention therfore also pertains to a composition comprising
  a) at least one compound that can be crosslinked under the action of an acid and/or
  b) at least one compound the solubility of which is altered under the action of an acid and
  c) as latent acid photoinitiator, at least one compound of the formulae I or II as described above.

These compositions may in addition to component c) comprise further photoinitiators, sensitizers and/or additives.

Resins which can be crosslinked by acid catalysis are, for example, mixtures of polyfunctional alcohols or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible.

In addition, oximesulfonates can be used, for example, as hardeners, which can be activated by light, for siloxane group-containing resins. Those resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. That type of polycondensation of polysiloxanes is described, for example, in J. J. Lebrun, H. Pode, Comprehensive Polymer Science, Vol. 5, p. 593, Pergamon Press, Oxford, 1989.

It is desirable in those reactions for the acid to be released when irradiated with light of various wavelength. Surprisingly, it has been found that these structurally new oximesulfonates are thermally and chemically stable and in addition capable of releasing the acid when irradiated with light. In addition they are bleached after exposure to light, a property which is very helpful for homogeneous generation of the acid throughout the entire thickness of the compositions irradiated by the light and which property is used for the curing of thick layers or the production of colourless articles with visible light.

Oximesulfonates can be used as hardeners, which can be activated by light, for acid-curable resins. Suitable acid-curable resins are all resins the curing of which can be accelerated by acid catalysts, such as aminoplasts or phenolic resole resins. Those resins are especially melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx/Lackkunstharze (Munich, 1971), pages 86 to 123 and 229 to 238, or in Ullmann/Encyclopädie der techn. Chemie, 4th Edition, Volume 15 (1978), pages 613 to 628, or Ullmann's Encyclopedia of Industrial Chemistry, Verlag Chemie, 1991, Vol. 18, 360 ff., Vol. A19, 371 ff.

The composition can for example be used as a surface coating. The surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. As already mentioned above, for example polysiloxanes can also be crosslinked using acid catalysis. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as α-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I or II. In that process, a) radical polymerisation initiators or b) photoinitiators can additionally be used. The former initiate polymerisation of the unsaturated groups during heat treatment, the latter during UV irradiation.

According to the invention, the compositions, which can be activated by light, may comprise further photoinitiators, sensitisers and/or additives in addition to component c), or the compounds of formula I or II can be used together with further photoinitiators, sensitisers and/or additives.

Examples of additional photoinitiators are radical photoinitiators, such as those from the class of the benzophenones, acetophenone derivatives, such as α-hydroxycycloalkylphenyl ketone, dialkoxyacetophenone, α-hydroxy- or α-amino-acetophenone, 4-aroyl-1,3-dioxolans, benzoin alkyl ethers and benzil ketals, monoacylphosphine oxides, bisacylphosphine oxides or titanocenes. Examples of especially suitable additional photoinitiators are: 1-(4-dodecylbenzoyl)-1-hydroxy-1-methyl-ethane, 1-(4-isopropylbenzoyl)-1-hydroxy-1-methyl-ethane, 1-benzoyl-1-hydroxy-1-methyl-ethane, 1-[4-(2-hydroxyethoxy)-benzoyl]-1-hydroxy-1-methylethane, 1-[4-(acryloyloxyethoxy)-benzoyl]-1-hydroxy-1-methyl-ethane, diphenyl ketone, phenyl-1-hydroxy-cyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthiobenzo-yl)-1-methyl-1-morpholino-ethane, benzil dimethyl ketal, bis(cyclopentadienyl)-bis(2,6-difluoro- 3-pyrryl-phenyl) titanium, trimethylbenzoyldiphenylphosphine oxide, bis(2,6-dimethoxybenzoyl)-(2,4,4-trimethyl-pentyl)-phosphine oxide, bis(2,4,6-trimethylbenzoyl)-2,4-dipentyloxyphenylphosphine oxide or bis(2,4,6-trimethylbenzoyl)phenylphosphine oxide. Further suitable additional photoinitiators are to be found in U.S. Pat. No. 4,950,581, column 20, line 35 to column 21, line 35. Other examples are trihalomethyltriazine derivatives or hexaarylbisimidazolyl compounds. Further examples for additional photoinitiators are borate compounds, as for example described in U.S. Pat. No. 4,772,530, EP 775706, GB 2307474, GB 2307473 and GB 2304472. The borate compounds preferably are used in combination with electron acceptor compounds, such as, for example dye cations, or thioxanthone derivatives.

Further examples of additional photoinitiators are, for example, peroxide compounds, e.g. benzoyl peroxide (other suitable peroxides are described in U.S. Pat. No. 4,950,581, column 19, lines 17–25) or cationic photoinitiators, such as aromatic sulfonium or iodonium salts, such as those to be found in U.S. Pat. No. 4,950,581, column 18, line 60 to column 19, line 10, or cyclopentadienyl-arene-iron(II) complex salts, for example ($\eta^6$-isopropylbenzene)($\eta^5$-cyclopentadienyl)-iron(II) hexafluorophosphate.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are
1. 2-(2'-Hydroxyphenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3', 5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(α, α-dimethylbenzyl)-2'-hydroxyphenyl)-benzotriazole, mixture of 2-(3'-tertbutyl-2'-hydroxy-5'-(2-octyloxycarbonylethyl)phenyl)-5-chloro-benzotriazole, 2-(3'-tert-butyl-5'-[2-(2-ethyl-hexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy) carbonyl-ethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl) phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$— wherein R=3'-tert-butyl-4'-hydroxy-5'-2H-benzotriazol-2-yl-phenyl.

2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.

4. Acrylates, such as α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

5. Sterically hindered amines, such as bis(2,2,6,6-tetramethyl-piperidyl)sebacate, bis(2,2,6,6-tetramethyl-piperidyl)succinate, bis(1,2,2,6,6-pentamethylpiperidyl) sebacate, nbutyl-3,5-di-tert-butyl-4-hydroxybenzyl-malonic acid bis(1,2,2,6,6-pentamethylpiperidyl) ester, condensation product of 1-hydroxyethyl-2,2,6,6-tetramethyl-4-hydroxypiperidine and succinic acid, condensation product of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl)

nitrilotriacetate, tetrakis(2,2,6,6-tetramethyl-4-piperidyl)-1, 2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]-decane-2,4-dione, bis(1-octyloxy-2,2,6,6-tetramethylpiperidyl) sebacate, bis(1-octyloxy-2,2,-6,6-tetramethylpiperidyl) succinate, condensation product of N,N'-bis(2,2,6,6-tetramethyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3-aminopropylamino)ethane, 8-a-cetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1 ,2,2,6,6-pentamethyl-4-piperidyl)-pyrrolidine-2,5-dione.

6. Oxalic acid diamides, such as 4,4'-dioctyloxy-oxanilide, 2,2'-diethoxy-oxanilide, 2,2'-di-octyloxy-5,5'-di-tert-butyl-oxanilide, 2,2'-didodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyl-oxanilide, mixtures of o- and p-methoxy- and of o- and p-ethoxy-di-substituted oxanilides.

7. 2-(2-Hydroxyphenyl)-1,3,5-triazines, such as 2,4,6-tris (2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-di-hydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl-/tridecyl-oxy-(2-hydroxypropyl)oxy-2-hydroxyphenyl]-4,6-bis(2,4-dimethylphenyl)-1,3,5-triazine.

8. Phosphites and phosphonites, such as triphenyl phosphite, diphenyl alkyl phosphates, phenyl dialkyl phosphites, tris(nonylphenyl) phosphite, trilauryl phosphite, trioctadecyl phosphite, distearyl-pentaerythritol diphosphite, tris(2,4-di-tert-butylphenyl) phosphite, diisodecylpentaerythritol diphosphite, bis(2,4-di-tert-butylphenyl) pentaerythritol diphosphite, bis(2,6-di-tert-butyl-4-methylphenyl)pentaerythritol diphosphite, bis-isodecyloxypentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the composition, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl-coumarines (as described e.g. in EP 624580), 3-(aroylmethylene)-thiazolines, thioxanthones, condensed aromatic compounds, such as perylene, aromatic amines (as described, for example, in U.S. Pat. No. 4,069, 954 or WO 96/41237) or cationic and basic colourants (as described, for example, in U.S. Pat. No. 4,026,705), for example eosine, rhodanine and erythrosine colourants, as well as dyes and pigments as described for example in JP 8320551-A, EP 747771, JP 7036179-A, EP 619520, JP 6161109-A, JP 6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, colourants, wetting agents or flow improvers.

For curing thick and pigmented coatings, the addition of micro glass beads or powdered glass fibres, as described in U.S. Pat. No. 5,013,768, is suitable.

Other examples of additional photoinitiators or additives have been given hereinbefore. Oximesulfonates can also be used, for example, in hybrid systems. Those systems are based on formulations that are full cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are, for example, radical full cure, oxidative crosslinking or humidity-initiated crosslinking. The second curing mechanism may be initiated purely thermally, if necessary with a suitable catalyst, or also by means of light using a second photoinitiator.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting on or immersion. When suitable surface coatings are used, electrical application, for example by electroimmersion coating, is also possible. After drying, the surface coating film is irradiated. If necessary, the surface coating film is then fully cured by means of heat treatment.

The compounds of formulae I or II can also be used for curing mouldings made from composites. A composite consists of a self-supporting matrix material, for example a glass fibre fabric, impregnated with the photocuring formulation.

Resist systems can be prepared by image-wise irradiation of systems comprising compounds of formulae I or II, followed by a developing step.

As already mentioned above, compounds of formulae I or II can be used as photosensitive acid donors in a photoresist.

The invention accordingly relates also to a photoresist based on oximesulfonates as photosensitive acid donors, the photoresist comprising as oximesulfonate a compound of formulae I or II.

The difference in solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive. If, on the other hand, those components reduce the solubility of the composition after irradiation, the resist is negative.

The invention accordingly relates also to a negative photoresist and to a positive photoresist.

The oximesulfonates of formulae I or II can also be used in chemically amplified resists. A chemically amplified photoresist is understood to be a resist composition the photosensitive component of which, when irradiated, provides only that amount of acid that is required to catalyse a chemical reaction of at least one acid-sensitive component of the resist, as a result of which the ultimate differences in solubility between irradiated and non-irradiated areas of the photoresist first develop.

The invention accordingly relates also to a chemically amplified photoresist.

Subject of the invention further is the use of a compound of the formula I or II as photosensitive acid donor in a photoresist.

Such resists exhibit an outstanding lithographic sensitivity to radiation of different wave-length, since compounds of formulae I or II can be easily tuned over a broad range of the electromagnetic spectrum. The photoresists according to the invention have excellent lithographic properties, especially a high sensitivity, and homogeneous exposure-conditions over the whole resist thickness due to the fact that the optical absorption is bleached upon irradiation.

Acid-sensitive components that produce a negative resist characteristic are especially compounds that, when catalysed by acid (the acid formed during irradiation of the compounds of formulae I or II), are capable of undergoing a crosslinking reaction with themselves and/or with one or more further components of the composition. Compounds of that type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of that type are generally known and are described, for example, in Ullmann's Encyclopädie der technischen Chemie, 4th Edition, Vol. 15 (1978), p. 613–628. The crosslinker components should generally be present in a concentration of from 2 to 40, preferably from 5 to 30, percent by weight, based on the total solids content of the negative composition.

Especially preferred as acid-curable resins are amino resins, such as non-etherified or etherified melamine, urea, guanidine or biuret resins, especially methylated melamine resins or butylated melamine resins, corresponding glycolurils and urones. There are to be understood by resins in this context both customary technical mixtures, which generally also comprise oligomers, and pure and high purity compounds. N-Methoxymethyl melamine and tetramethoxymethyl glucoril and N,N'-dimethoxymethylurone are the acid-curable resins given the greatest preference.

The concentration of the compound of formula I or II in negative resists is in general from 0.1 to 30, preferably up to 20, percent by weight, likewise based on the total solids content of the compositions. From 1 to 15 percent by weight is especially preferred.

Where appropriate, the negative compositions may additionally comprise a film-forming polymeric binder. That binder is preferably an alkali-soluble phenolic resin. Well suited for that purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis( 4-hydroxyphenyl) propane. Also suitable are homo- and co-polymers based on ethylenically unsaturated phenols, for example homopolymers of vinyl- and 1-propenyl-substituted phenols, such as p-vinylphenol or p-(1-propenyl)phenol or copolymers of those phenols with one or more ethylenically unsaturated materials, for example styrenes. The amount of binder should generally be from 30 to 95 percent by weight or, preferably, from 40 to 80 percent by weight.

The invention thus includes, as a special embodiment, as already mentioned above, negative, alkali-developable photoresists, comprising an oximesulfonate of formula I or II as described above, an alkali-soluble phenolic resin as binder and a component that when catalysed by an acid undergoes a crosslinking reaction with itself and/or with the binder.

An especially preferred form of that negative resist comprises from 1 to 15 percent by weight oximesulfonate, from 40 to 99 percent by weight of a phenolic resin as binder, for example one of those mentioned above, and from 0.5 to 30 percent by weight of a melamine resin as crosslinking agent, the percentages relating to the solids content of the composition. With novolak or especially with polyvinyl phenol as binder, a negative resist having especially good properties is obtained.

Oximesulfonates can also be used as acid generators, which can be activated photochemically, for the acid-catalysed crosslinking of, for example, poly(glycidyl) methacrylates in negative resist systems. Such crosslinking reactions are described, for example, by Chae et al. in Pollimo 1993, 17(3), 292.

Monomeric or polymeric compounds that are alkali-insoluble but are cleaved in the presence of acid, or are capable of being rearranged intramolecularly, in such a manner that reaction products remain that are soluble in a customary alkaline developer and/or that cause an otherwise alkali-insoluble and acid-resistant additional binder to become soluble in the developer, produce a positive characteristic in photoresist compositions according to the invention. Substances of that type are referred to hereinafter as solution inhibitors.

As already indicated hereinbefore, the invention therefore includes, as a further special embodiment, positive alkaline-developable photoresists, comprising a compound of formula I or II and at least one compound that substantially prevents the composition from dissolving in an alkaline developer, but that can be cleaved in the presence of an acid in such a manner that reaction products remain that are soluble in the developer and/or that cause an acid-resistant additional binder that would otherwise be virtually insoluble in the developer to dissolve in the developer.

There may be used as solution inhibitors monomeric and polymeric organic compounds having functional groups that would be soluble per se in an alkaline medium, for example aromatic hydroxy groups, carboxylic acid groups, secondary amino groups and keto or aldehyde groups, but that have been chemically so altered by reaction with a suitable compound that they are insoluble in aqueous alkali, the protecting groups formed in the mentioned reaction being capable of being cleaved again by acid catalysis in such a manner that the functional groups are recovered in their original form.

For the protection of hydroxy groups, carboxylic acid groups or secondary amino groups there are suitable, for example, dihydrofuran or 3,4-dihydropyran and the derivatives thereof, benzyl halides, alkyl halides, haloacetic acid, haloacetic acid esters, chlorocarbonic acid esters, alkylsulfonyl halides, aromatic sulfonyl halides, dialkyl dicarbonates or trialkylsilyl halides, it being possible for the reactions to form the protected derivatives to be carried out in known manner. Customary conversion into ketals and acetals is suitable for protecting keto and aldehyde groups.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

In positive resists of the mentioned type a film-forming, polymeric solution inhibitor can either be the only binder in the photoresist or can be used in admixture with an acid-inert binder and, where appropriate, a monomeric solution inhibitor.

Examples of acid-inert binders are novolaks, especially those based on o-, m- or p-cresol and formaldehyde, also poly(p-hydroxystyrene), poly(p-hydroxy-α-methylstyrene) and copolymers of p-hydroxystyrene, p-hydroxy-α-methylstyrene and acetoxystyrene.

Examples of polymeric solution inhibitors are novolaks, especially those based on o-, m- or p-cresol and formaldehyde, poly(p-hydroxystyrene), poly(p-hydroxy-α-methylstyrene), copolymers of p-hydroxystyrene or p-hydroxy-α-methylstyrene and acetoxystyrene or acrylic acid and/or methacrylic acid and (meth)acrylic acid esters, which are reacted in known manner with dihydrofuran, 3,4-dihydropyran, benzyl halides, alkyl halides, haloacetic acid, haloacetic acid esters, chlorocarbonic acid esters, alkylsulfonyl halides, aromatic sulfonyl halides, dialkyl dicarbonate or trialkylsilyl halides. Also suitable are polymers of p-(2-tetrahydropyranyl)-oxystyrene or p-(tert-butyloxycarbonyl)-oxystyrene with (meth)acrylic acid, (meth)acrylic acid esters and/or p-acetoxystyrene and polymers of p-hydroxystyrene and/or p-(2-tetrahydropyranyl)-oxystyrene with 3-hydroxybenzyl (meth)acrylates, which can, if necessary, additionally be protected by reaction with one of the compounds listed above.

Especially suitable are polymers that are—depending on the light sources used for irradiation—transparent in the wavelength range used for irradiation. Wavelengths can vary between 180 and 1500 nm. The polymers can carry both, groups that, after acid-catalysed deprotecting, bring about a change in solubility, and hydrophobic and hydrophilic groups that increase the solubility of the acid generator and ensure aqueous-alkaline developability. Examples of such polymers are acrylates and methacrylates prepared by co-, ter-, or quater-polymerisation from the corresponding monomers like methyl (meth)acrylate, (meth)acrylic acid, tert-butyl (meth)acrylate, 3-oxocyclohexyl (meth)acrylate, tetrahydropyranyl (meth)acrylate, adamantyl (meth)acrylate, cyclohexyl (meth)acrylate, norbornyl (meth)acrylate. The monomers can also combine two of above mentioned structures like for example (2-tetrahydropyranyl)-oxynorbonylalcohol acrylates or (2-tetrahydropyranyl) oxymethyltricyclododecanemethanol methacrylates. Examples for such monomers are given in U.S. Pat. No. 5,621,019. The monomers may also carry organosilicon radicals in order, for example, to further increase the resistance in the case of dry etching processes, like for example trimethylsilylmethyl (meth)acrylate.

The invention accordingly also relates to a chemically amplified positive resist comprising as photosensitive acid donor a compound of formula I or II.

The invention relates also to a photoresist comprising polymers that are transparent down to the wavelength region of 180 nm.

A special embodiment of the positive resist according to the invention comprises from 75 to 99.5 percent by weight of a film-forming polymer that contains protecting groups that can be removed by acid catalysis, and from 0.5 to 25 percent by weight of oximesulfonates of formula I or II, the percentages being based on the solids content of the compositions. In this context, preference is given to compositions comprising from 80 to 99 percent by weight of the mentioned polymer and from 1 to 20 percent by weight of oximesulfonate.

Another embodiment is a positive resist comprising from 40 to 90 percent by weight of an acid-inert film-forming polymer as binder, from 5 to 40 percent by weight of a monomeric or polymeric compound having protecting groups removable by acid catalysis and from 0.5 to 25 percent by weight of oximesulfonates of formula I or II, the percentages relating to the solids content of the compositions. Of those compositions, preference is given to those comprising from 50 to 85 percent by weight acid-inert binder, from 10 to 30 percent by weight monomeric or polymeric solution inhibitor and from 1 to 15 percent by weight oximesulfonates.

Oximesulfonates can also be used as solubility enhancers, which can be activated by light. In that case, the compounds are added to a film-forming material comprising substantially no components that polymerise with the oximesulfonic acid ester when heated or when irradiated with actinic radiation. However, the oximesulfonates reduce the speed at which the film-forming material dissolves in a suitable developer medium. That inhibiting effect can be cancelled by irradiating the mixture with actinic radiation, so that a positive image can be produced. Such an application is described, for example, in EP 241423.

A further special embodiment of the invention is, finally, a positive resist comprising a compound of formula I or II and a binder that is virtually insoluble in an alkaline developer and that becomes soluble in the developer in the presence of the photolysis products of the compound of formula I or II. In this case the amount of the mentioned oximesulfonate compound is generally from 5 to 50 percent by weight, based on the solids content of the composition.

The use of the oximesulfonates according to the invention in chemically amplified systems, which operates on the principle of the removal of a protecting group from a polymer, generally produces a positive resist. Positive resists are preferred to negative resists in many applications, especially because of their greater resolution. There is, however, also interest in producing a negative image using the positive resist mechanism, in order to combine the advantages of the high degree of resolution of the positive resist with the properties of the negative resist. That can be achieved by introducing a so-called image-reversal step as described, for example, in EP 361906. For that purpose, the image-wise irradiated resist material is treated, before the developing step, with, for example, a gaseous base, the acid that has been produced image-wise being neutralised. Then, a second irradiation, over its whole area, and thermal after treatment are carried out and the negative image is then developed in the customary manner.

In addition to the mentioned constituents, both the negative and the positive photoresist compositions may additionally comprise one or more of the additives customarily used in photoresists in the amounts familiar to a person skilled in the art, for example flow improvers, wetting agents, adhesives, thixotropic agents, colourants, pigments, fillers, solubility accelerators and so on. The reaction can be accelerated by the addition of photosensitisers which shift and/or broaden the spectral sensitivity. These are especially for example aromatic carbonyl compounds, such as benzophenone, thioxanthone, anthraquinone and 3-acylcoumarin derivatives and also 3-(aroylmethylene) thiazolines, but also eosine, rhodanine and erythrosine colourants.

Other compounds that accelerate the acid formation or enhance the acid concentration may also be used in combination with the oximesulfonates of the formulae I or II according to the invention in positive or negative resists or imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

For application, the compositions must generally also comprise a solvent. Examples of suitable solvents are ethyl acetate, 3-methoxymethyl propionate, ethyl pyruvate, 2-heptanone, diethyl glycol dimethyl ether, cyclopentanone, cyclohexanone, γ-butyrolactone, ethyl methyl ketone, 2-ethoxyethanol, 2-ethoxyethyl acetate and especially 1-methoxy-2-propyl acetate. The solvent may also be in the form a mixture, for example of two or more of the above-mentioned solvents. The choice of solvent and the concentration depend, for example, on the nature of the composition and on the coating method.

The solution is uniformly applied to a substrate by means of known coating methods, for example by spin-coating, immersion, knife coating, curtain pouring techniques, brush application, spraying and reverse roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 μm to more than 100 μm.

Possible areas of use of the composition according to the invention are as follows: use as photoresists for electronics, such as etching resists, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

After the coating operation, the solvent is generally removed by heating, resulting in a layer of the photoresist on the substrate. The drying temperature must of course be lower than the temperature at which certain components of the resist might be thermally cured. Care must be taken in that respect especially in the case of negative photoresists. In general, drying temperatures should not exceed from 80 to 130° C.

The resist coating is then irradiated image-wise. The expression "image-wise irradiation" includes irradiation in a predetermined pattern using actinic radiation, i.e. both irradiation through a mask containing a predetermined pattern, for example a transparency, and irradiation using a laser beam that is moved over the surface of the coated substrate, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 p 275–281 and by K. P. Nicolay in Offset Printing 1997, 6, p 34–37.

After the irradiation and, if necessary, thermal treatment, the unirradiated sites (in the case of positive resists) or the irradiated sites (in the case of negative resists) of the composition are removed in a manner known per se using a developer.

It is generally necessary to allow a certain period of time prior to the developing step in order to allow the acid-sensitive components of the resist composition to react. In order to accelerate that reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 150° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may be used, for example, for the developing. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n- propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5N, but are usually diluted in suitable manner before use. For example solutions having a normality of approximately 0.1 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of those solvents. A typical aqueous/organic developer system is based on Butylcellosolvel®/water.

It is known from EP 592139 that oximesulfonates can be used as acid generators, which can be activated by light in compositions that are suitable for the surface treatment and cleaning of glass, aluminium and steel surfaces. The use of those compounds in such organosilane systems results in compositions that have significantly better storage stability than those obtained when the free acid is used.

Oximesulfonates can also be used to produce so-called "print-out" images when the compound is used together with a colourant that changes colour when the pH changes, as described e.g. in Japanese Patent Application JP Hei 4 328552-A or in U.S. Pat. No. 5,237,059. Such co-our-change systems can be used according to EP 199672 also to monitor goods that are sensitive to heat or radiation. In addition the newly claimed compounds of formula I or II exhibit already a colour change on their own when they are exposed to light of suitable wave-length. This color-change must not be as pronounced as in the case of using it in combination with the before mentioned acid-sensitive colourants, but it is well visible.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with oximesulfonates can be used as light indicators or simple throw away dosimeters. Especially for light, that is invisible to the human eye, like UV- or IR-light, such dosimeters are of interest.

The oximesulfonates of the present invention can also be used to shape polymers that undergo an acid induced transition into a state where they have the required properties using photolithography. For instance the oximesulfonates can be used to pattern conjugated emissive polymers as described in M. L. Renak; C. Bazan; D. Roitman; Advanced materials 1997, 9, 392. Such patterend emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coating, insulating layers and buffer layers in the production of microchips and printed circuit boards.

The formulations may also be used as conformal coatings, photoimagable dielectricas as they are used in sequential build up systems for printed cricuit boards, stress buffer layers and isolation layers in the manufacturing of computer chips.

It is known that conjugated polymers like, e.g. polyanilines can be converted from semiconductive to conductive state by means of proton doping. The oxime-sulfonates of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable for the crosslinking of compositions comprising compounds of formula I or II are radiation sources that emit radiation of a wavelength of approximately from 150 to 1500, for example from 180 to 1000 or preferably from 240 to 700 nanometers. Both point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the lamp and the substrate according to the invention to be irradiated can vary, for example, from 2 cm to 150 cm, according to the intended use and the type and/or strength of the lamp. Suitable light sources are therefore especially mercury vapour lamps, especially medium and high pressure mercury lamps, from the radiation of which emission lines at other wavelengths can, if desired, be filtered out. That is especially the case for relatively short wavelength radiation. The distance between the lamp and the workpiece can vary, for example, from 2 cm to 150 cm, according to the intended use and the type and/or strength of the lamp. It is, however, also possible to use low energy lamps (for example fluorescent tubes) that are capable of emitting in the appropriate wavelength range. An example thereof is the Phillps TLO3 lamp. Another type of light soure that can be used are the light emitting diodes (LED) that emitt at different wavelength throughout the whole spectrum either as small band emitting source or as broad band (white light) source. Also suitable are laser light sources, for example excimer lasers, such as Kr-F lasers for irradiation at 248 nm or Ar-F lasers at 193 nm. Lasers in the visible range and in the infrared range can also be used. Very especially suitable is radiation of the mercury h and g lines at wavelengths of 436 and 405 nanometers. A suitable laser-beam source is, for example, the argon-ion laser, which emits radiation at wavelengths of 454, 458, 466, 472, 478, 488 and 514 nanometers. Nd-YAG-lasers emitting light at 1064 nm and it's second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the oximesulfonate in the composition in the irradiated sections of the surface coating decomposes to form sulfonic acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The compounds of formulae I or II are generally added to the compositions in an amount from 0.1 to 30 % by weight, for example from 0.5 to 10 % by weight, especially from 1 to 5 % by weight.

Subject of the invention is a method of crosslinking compounds that can be crosslinked under the action of an acid, which method comprises adding a compound of formula I and/or II according to claim 1 to the above-mentioned compounds and irradiating imagewise or over the whole area with light having a wavelength of 180–1500 nm.

The invention relates also to the use of compounds of formulae I or II as photosensitive acid donors in the preparation of surface coatings, printing inks, printing plates, dental compositions, colour filters, resist materials or image-recording materials, or image-recording materials for recording holographic images, as well as to a method for the preparation of surface coatings, printing inks, printing plates, dental compositions, colour filters, resist materials and as image-recording material, or image-recording material for recording holographic images, which comprises irradiating a composition according to the invention with light having a wavelength of 180–1500 nm.

The invention further pertains to the use of a composition as described above for the preparation of surface coatings, printing inks, printing plates, dental compositions, colour filters, resist materials and as image-recording material, or image-recording material for recording holographic images.

The examples which follow illustrate the invention in more detail. Parts and percentages, as in the remainder of the description and in the claims, are by weight unless indicated otherwise.

EXAMPLE 1

(4-Methylsulfonyloxyimino-cyclohexa-2,5-dienylidene)-phenyl-acetonitrile 1.1: (4-Hydroxyimino-cyclohexa-2,5-dienylidene)-phenyl-acetonitrile 60 g of KOH are dissolved in 300 ml of methanol and heated up to 55° C. To the solution are added 32.2 g (0.27 mol) of phenylacetonitrile followed by 30.8 g (0.25 mol) of nitrobenzene. The reaction mixture is stirred at 55° C. for 4 hrs. After cooling, 400 ml of water are added with stirring. The resulting solution is acidified by addition of 110 ml of acetic acid in 100 ml of water, leading to a yellow-orange precipitate. The mixture is then filtered, and the yellow solid is washed with a mixture of methanol and water. The crude product is dried in air, boiled with 150 ml of benzene for 15 min., cooled, filtered and dried under vacuum. 42.6 g (77%) of (4-Hydroxyimino-cyclohexa-2,5-dienylidene)-phenyl-acetonitrile are obtained in the form of a yellow solid having a melting point of 159–163° C. (dec.).

1.2: (4-Methylsulfonyloxyimino-cyclohexa-2,5-dienylidene)-phenyl-acetonitrile 10 g (45 mmol) of (4-Hydroxyimino-cyclohexa-2,5-dienylidene)-phenyl-acetonitrile are dissolved in 100 ml of tetrahydrofuran (THF) and cooled in an ice bath. After adding 9.41 ml (68 mmol) of triethylamine to the solution, 3.83 ml (50 mmol) of methanesulfonyl chloride are added dropwise, keeping the temperature below 5° C. The reaction mixture is gradually warmed to room temperature, and stirred for 1 hr. The reaction mixture is poured into 200 ml of water, and extracted with ethyl acetate. The organic phase is washed with hydrochloric acid solution, water, and sodium chloride solution. The organic phase is dried over $MgSO_4$, the solvent is distilled off, and the residue is purified by recrystallization from toluene. 9.4 g (70%) of (4-Methylsulfonyloxyimino-cyclohexa-2,5-dienylidene)-phenyl-acetonitrile are obtained in the form of a yellow-green crystal having a melting point of 137–139° C. (dec.). $^1$H-NMR shows that the product is a 82:18 mixture of the E and Z isomers (two dxd signals for H-C(2 or 6) at 6.78 and 6.91 ppm.

EXAMPLE 2

(4-Methylsulfonyloxyimino-cyclohexa-2,5-dienylidene)-(4-methoxyphenyl)-acetonitrile 2.1: (4-Hydroxyimino-cyclohexa-2,5-dienylidene)-(4-methoxyphenyl)-acetonitrile 80 g of KOH are dissolved in 400 ml of methanol and heated up to 55° C. To the solution are added 50 ml (0.37 mol) of p-methoxyphenylacetonitrile, followed by 35 ml (0.34 mol) of nitrobenzene. The reaction mixture is stirred at 55° C. for 4 hrs. After cooling, 500 ml of water are added with stirring. The resulting solution is acidified by addition of 110 ml of acetic acid in 100 ml of water, leading to a precipitate. The mixture is then filtered, and the solid is washed with a mixture of methanol and water. The crude product is dried in air and recrystallized from 500 ml of ethyl acetate. 45.6 g (53%) of (4-Hydroxyimino-cyclohexa-2,5-dienylidene)-(4-methoxyphenyl)-acetonitrile are obtained in the form of orange crystals having a melting point of 161–163° C. (dec.).

2.2: (4-Methylsulfonyloxyimino-cyclohexa-2,5-dienylidene)-(4-methoxyphenyl)-acetonitrile 15 g (59 mmol) of (4-Hydroxyimino-cyclohexa-2,5-dienylidene)-(4-methoxyphenyl)-acetonitrile are dissolved in 200 ml of THF and cooled in an ice bath. After adding 12.4 ml (89 mmol) of triethylamine to the solution, 5.03 ml (65 mmol) of methanesulfonyl chloride are added dropwise, keeping the temperature below 5° C. The reaction mixture is gradually warmed to room temperature, and stirred for 1 hr. The reaction mixture is poured into 300 ml of water, and extracted with ethyl acetate. The organic phase is washed with hydrochloric acid solution, water, and sodium chloride solution. The organic phase is dried over $MgSO_4$, the solvent is distilled off, and the residue is purified by recrystallization from ethyl acetate. 6.8 g (35%) of (4-Methylsulfonyloxyimino-cyclohexa-2,5-dienylidene)-(4-methoxyphenyl)-acetonitrile are obtained in the form of orange crystals having a melting point of 161–162l° C. (dec.).

EXAMPLE 3

(4-Methylphenyisulfonyloxyimino-cyclohexa-2,5-dienylidene)-(4-methoxyphenyl)-acetonitrile 10 g (40 mmol) of (4-Hydroxyimino-cyclohexa-2,5-dienylidene)-(4-methoxyphenyl)-acetonitrile (prepared according to the method of example 2.1) are dissolved in 80 ml of THF and cooled in an ice bath. After adding 8.3 ml (60 mmol) of triethylamine to the solution, 8.3 g (44 mmol) of p-toluenesulfonyl chloride dissolved in 20 ml of THF are added dropwise, keeping the temperature below 5° C. The reaction mixture is gradually warmed to room temperature, and stirred for 1 hr. The reaction mixture is poured into 200 ml of water, and extracted with ethyl acetate. The organic phase is washed with hydrochloric acid solution, and sodium chloride solution. The organic phase is dried over $MgSO_4$, the solvent is distilled off, and the residue is purified by recrystallization from toluene. 9.4 g (58%) of (4-methylphenylsulfonyl-oxyimino-cyclohexa-2,5-dienylidene)-(4-methoxyphenyl)-acetonitrile are obtained in the form of a brown crystal having a melting point of 129–136° C. (dec.).

EXAMPLE 4

(4-Methylsultonyloxyimino-cyclohexa-2,5-dienylidene)-(4-methylphenyl)-acetonitrile 4.1: (4-Hydroxyimino-cyclohexa-2,5-dienylidene)-(4-methylphenyl)-acetonitrile 40 g of KOH are dissolved in 200 ml of methanol and heated up to 55° C. To the solution are added 25 g (0.19 mol) of 4-methylphenylacetonitrile, followed by 18 ml (0.17 mol) of nitrobenzene. The reaction mixture is stirred at 55° C. for 2.5 hrs. After cooling, 400 ml of water are added with stirring. The resulting solution is acidified by addition of 110 ml of acetic acid in 100 ml of water, leading to a yellow precipitate. The mixture is then filtered, and the solid is washed with a mixture of methanol and water, and methanol. After the solid is dried in air, 29.6 g (74%) of (4-Hydroxyimino-cyclohexa-2,5-dienylidene)-(4-methylphenyl)-acetonitrile are obtained in the form of a yellow powder having a melting point of 148–151° C. (dec.).

4.2 : (4-Methylsulfonyloxyimino-cyclohexa-2,5-dienylidene)-(4-methylphenyl)-acetonitrile 10 g (42 mmol) of (4-Hydroxyimino-cyclohexa-2,5-dienylidene)-(4-methylphenyl)-acetonitrile are dissolved in 80 ml of THF and cooled in an ice bath. After adding 8.8 ml (63 mmol) of triethylamine to the solution, 3.6 ml (47 mmol) of methanesulfonyl chloride are added dropwise, keeping the temperature below 5° C. The reaction mixture is stirred in the ice bath for 30 min. The reaction mixture is poured into 200 ml of water, and extracted with ethyl acetate. The organic phase is washed with hydrochloric acid solution, water, and sodium chloride solution. The organic phase is dried over $MgSO_4$, the solvent is distilled off, and the residue is purified by recrystallization from toluene. 4.6 g (35%) of (4-Methylsulfonyloxyimino-cyclohexa-2,5-dienylidene)-(4-methylphenyl)-acetonitrile are obtained in the form of yellow crystals having a melting point of 139–141° C. (dec.).

EXAMPLE 5

(4-Methylsulfonyloxyimino-cyclohexa-2,5-dienylidene)-(3-methylphenyl)-acetonitrile 5.1: (4-Hydroxyimino-cycohexa-2,5-dienylidene)-(3-methylphenyl)-acetonitrile 40 g of KOH are dissolved in 300 ml of methanol and heated up to 55° C. To the solution are added 25 g (0.19 mol) of 3-methylphenylacetonitrile followed by 18 ml (0.17 mol) of nitrobenzene. The reaction mixture is stirred at 55° C. for 4 hrs. After cooling, 400 ml of water are added with stirring. The resulting solution is acidified by addition of 110 ml of acetic acid in 100 ml of water, leading to a yellow precipitate. The mixture is then filtered, and the solid is washed with a mixture of methanol and water, and methanol. After the solid is dried in air, 26.9 g (67%) of (4-Hydroxyimino-cyclohexa-2,5-dienylidene)-(3-methylphenyl)-acetonitrile are obtained in the form of a yellow powder having a melting point of 146–149° C. (dec.).

5.2: (4-Methylsulfonyloxyimino-cyclohexa-2,5-dienylidene)-(3-methylphenyl)-acetonitrile 25 g (0.11 mol) of (4-Hydroxyimino-cyclohexa-2,5-dienylidene)-(3-methylphenyl)-acetonitrile are dissolved in 150 ml of THF and cooled in an ice bath. After adding 22 ml (0.16 mol) of triethylamine to the solution, 9.0 ml (0.12 mol) of methanesulfonyl chloride are added dropwise, keeping the temperature below 5° C. The reaction mixture is stirred in the ice bath for 30 min. The reaction mixture is poured into 200 ml of water, and extracted with ethyl acetate. The organic phase is washed with hydrochloric acid solution, water, and sodium chloride solution. The organic phase is dried over $MgSO_4$, the solvent is distilled off, and the residue is purified by recrystallization from toluene. 16.8 g (51%) of (4-Methylsulfonyloxyimino-cyclohexa-2,5-dienylidene)-(3-methylphenyl)-acetonitrile are obtained in the form of yellow crystals having a melting point of 159–161° C. (dec.).

EXAMPLE 6

(4-Methylsulfonyloxyimino-cyclohexa-2,5-dienylidene)-(3,4-dimethylphenyl)-acetonitrile 6.1: (4-Hydroxyimino-cyclohexa-2,5-dienylidene)-(3,4-dimethylphenyl)-acetonitrile 46 g (0.30 mol) of 3,4-dimethylphenylacetonitrile (containing 30% of 2,3-dimethylphenylacetonitrile) are dissolved in 200 ml of DMSO. To the solution are added 22 g (0.45 mol) of NaCN, and the mixture is stirred at room temperature overnight. The reaction mixture is poured into 400 ml of water, and extracted with ethyl acetate. The organic phase is washed with water, and sodium chloride solution. The organic phase is dried over $MgSO_4$, the solvent is distilled off, and 42.5 g of liquid is obtained. 20 g of this liquid is added to 200 ml of methanol containing 30 g of KOH, followed by adding 12.9 ml (0.13 mol) of nitrobenzene. The mixture is stirred at 55° C. for 8 hrs. After cooling, 400 ml of water are added with stirring. The resulting solution is acidified by addition of 110 ml of acetic acid in 100 ml of water, leading to a precipitate. The mixture is then filtered, and the solid is washed with a mixture of methanol and water, and methanol. The crude product is dried in air, boiled with 300 ml of toluene for 1 hr, cooled, filtered and dried under vacuum. 12.5 g of (4-Hydroxyimino-cyclohexa-2,5-dienylidene)-(3,4-dimethylphenyl)-acetonitrile are obtained in the form of a yellow powder having a melting point of 175–177° C. (dec.). $^1$H-NMR and $^{13}$C-NMR measurements indicate, that the obtained compound does not contain any 2,3-dimethyl isomer.

6.2: (4-Methylsulfonyloxyimino-cyclohexa-2,5-dienylidene)-(3,4-dimethylphenyl)-acetonitrile 10 g (40 mmol) of (4-Hydroxyimino-cyclohexa-2,5-dienylidene)-(3,4-dimethylphenyl)-acetonitrile are dissolved in 160 ml of THF and cooled in an ice bath. After adding 8.4 ml (60 mmol) of triethylamine to the solution, 3.4 ml (44 mmol) of methanesulfonyl chloride are added dropwise, keeping the temperature below 5° C. The reaction mixture is stirred in the ice bath for 30 min. The reaction mixture is poured into 150 ml of water, and extracted with ethyl acetate. The organic phase is washed with hydrochloric acid solution, water, and sodium chloride solution. The organic phase is dried over MgSO$_4$, the solvent is distilled off, and the residue is purified by recrystallization from toluene. 9.3 g (71%) of (4-methylsulfonyloxyiminocyclohexa-2,5-dienylidene)-(3,4-dimethylphenyl)-acetonitrile are obtained in the form of yellow crystals having a melting point of 131–133° C. (dec.).

EXAMPLE 7

(4-Methylsulfonyloxyimino-cyclohexa-2,5-dienylidene)-thiophen-2-yl-acetonitrile 7.1: (4-Hydroxyimino-cyclohexa-2,5-dienylidene)-thiophen-2-yl-acetonitrile 9.5 g of KOH are dissolved in 50 ml of methanol. To the solution are added 5 g (41 mmol) of thiophene-2-acetonitrile followed by 4.2 ml (41 mmol) of nitrobenzene. After the reaction mixture is stirred at room temperature for 2 hrs, 200 ml of water are added with stirring. The resulting solution is acidified by addition of 30 ml of acetic acid in 25 ml of water, leading to a dark orange precipitate. The mixture is then filtered, and the solid is washed with a mixture of methanol and water, and methanol. The crude product is dried in air and recrystallized from toluene. 4.7 g (50%) of (4-Hydroxyimino-cyclohexa-2,5-dienylidene)-thiophen-2-yl-acetonitrile are obtained in the form of a dark orange powder having a melting point of 151–155° C. (dec.).

7.2: (4-Methylsulfonyloxyimino-cyclohexa-2,5-dienylidene)-thiophen-2-yl-acetonitrile 4.5 g (20 mmol) of (4-Hydroxyimino-cyclohexa-2,5-dienylidene)-thiophen-2-yl-acetonitrile are dissolved in 50 ml of THF and cooled in an ice bath. After adding 4.2 ml (30 mmol) of triethylamine to the solution, 1.7 ml (22 mmol) of methanesulfonyl chloride are added dropwise, keeping the temperature below 5° C. The reaction mixture is stirred in the ice bath for 30 min. The reaction mixture is poured into 200 ml of water, and extracted with ethyl acetate. The organic phase is washed with hydrochloric acid solution, water, and sodium chloride solution. The organic phase is dried over MgSO$_4$, the solvent is distilled off, and the residue is purified by recrystallization from toluene. 1.8 g (30%) of (4-Methylsulfonyloxyimino-cyclohexa-2,5-dienylidene)-thiophen-2-yl-acetonitrile are obtained in the form of orange crystals having a melting point of 123–125° C. (dec.).

EXAMPLE 8

(5-Methylsulfonyloxyimino-5H-thiophen-2-ylidene)-phenyl-acetonitrile 8.1: (5-Hydroxyimino-5H-thiophen-2-ylidene)-phenyl-acetonitrile 14 g of KOH are dissolved in 50 ml of methanol. To the solution are added 7.1 ml (62 mmol) of phenylacetonitrile followed by 10 g (62 mmol) of 2-nitrothiophene dissolved in 30 ml of methanol. After the reaction mixture is stirred in the ice bath for 10 min, 200 ml of water are added with stirring. The resulting solution is acidified by addition of 55 ml of acetic acid in 50 ml of water, and extracted with ethyl acetate. The organic phase is washed with sodium chloride solution, and dried over MgSO$_4$. After the solvent is distilled off, the residue is purified by means of column chromatography on silica gel with ethyl acetate-hexane (1:3), and recrystallization from toluene. 5.3 g (38%) of (5-Hydroxyimino-5H-thiophen-2-ylidene)-phenyl-acetonitrile are obtained in the form of orange crystals having a melting point of 165° C. (dec.).

8.2: (5-Methylsulfonyloxyimino-5H-thiophen-2-ylidene)-phenyl-acetonitrile 5 g (22 mmol) of (5-Hydroxyimino-5H-thiophen-2-ylidene)-phenyl-acetonitrile are dissolved in 50 ml of THF and cooled in an ice bath. After adding 4.6 ml (33 mmol) of triethylamine to the solution, 1.9 ml (24 mmol) of methanesulfonyl chloride are added dropwise, keeping the temperature below 5° C. The reaction mixture is stirred while cooling in an ice bath for 30 min. The reaction mixture is poured into 200 ml of water, and extracted with ethyl acetate. The organic phase is washed with hydrochloric acid solution and sodium chloride solution. The organic phase is dried over MgSO$_4$, the solvent is distilled off, and the residue is purified by recrystallization from toluene. 5.2 g (77%) of (5-Methylsulfonyloxyimino-5H-thiophen-2-ylidene)-phenyl-acetonitrile are obtained in the form of greenish brown crystals having a melting point of 160–162° C. (dec.).

EXAMPLE 9

(4-Methylsulfonyloxyimino-3-methylcyclohexa-2,5-dienylidene)-phenyl-acetonitrile 9.1: (4-Hydroxyimino-3-methyl-cyclohexa-2,5-dienylidene)-phenylacetonitrile 39.6 g of KOH (0.6 mol, assay 85%) are dissolved in 200 ml of methanol and heated up to 55° C. To the solution are added 23.4 g (0.20 mol) of phenylacetonitrile, followed by 25 g (0.18 mol) of o-nitrotoluene. The dark red reaction mixture is stirred at 55° C. for 4 hrs. After cooling, the mixture is poured into 500 ml of water, and acidified by addition of 60 ml of acetic acid. The resulting orange precipitate is filtered, washed with water, methanol:water 1:1 (v/v), and dried under vacuum. The crude product (16.8 g, 40%) has a melting point of 161–164° C. (dec) (Lit: 161° C. dec; J. Org. Chem. 26, 4270, 1961) and is used in the next step without further purification.

9.2: (4-Methylsulfonyloxyimino-3-methylcyclohexa-2,5-dienylidene)-phenyl-acetonitrile 16.7 g (70 mmol) of crude (4-Hydroxyimino-3-methyl-cyclohexa-2,5-dienylidene)-phenylacetonitrile are dissolved in 100 ml of THF and cooled in an ice bath. After adding 6.0 ml (77 mmol) of methanesulfonyl chloride, 14.8 ml (106 mmol) of triethylamine are added dropwise to the solution, keeping the temperature below 10° C. The reaction mixture is stirred in the ice bath for 30 min., poured into 250 ml of iced water, and extracted with ethyl acetate. The organic phase is washed with 0.2 N hydrochloric acid, water, and saturated aqueous sodium chloride. The organic phase is dried over $MgSO_4$, the solvent is distilled off, and the residue is purified by recrystallization from toluene. 11.5 g (52%) of (3-Methyl-4-methylsulfonyloxyimino-cyclohexa-2,5-dienylidene)-phenyl-acetonitrile are obtained in the form of bright yellow crystals having a melting point of 136–138° C.(dec.).

Elemental analysis ($C_{16}H_{14}N_2O_3S$): calc.: C 61.13% H 4.49% N 8.91% found: C 61.18% H 4.49% N 8.80%

EXAMPLE 10

(4-Methylsulfonyloxyimino-3-methoxycyclohexa-2,5-dienylidene)-phenyl-acetonitrile 10.1: (4-Hydroxyimino-3-methoxy-cyclohexa-2,5-dienylidene)-phenylacetonitrile 21.0 g (0.18 mol) of phenylacetonitrile and 25 g (0.16 mol) of o-nitroanisole are added at 25° C. to a solution of 35.6 g KOH (0.54 mol, assay 85%) in 180 ml of methanol and the dark red reaction mixture is stirred at 55° C. for 6 hrs. After cooling, the mixture is diluted with 500 ml of water, and acidified by addition of 60 ml of acetic acid with cooling. The resulting orange precipitate is filtered, washed with water, methanol:water 1:1 (v/v), and dried at 80° C. under vacuum. The crude product (30.8 g, 75%) has a melting point of 180–182° C. (dec) (Lit: 187° C. dec; J. Org. Chem. 26, 4270, 1961) and is used in the next step without further purification. The $^1$H-NMR spectrum indicates the presence of two isomers in nearly 1:1 ratio.

10.2: (4-Methylsulfonyloxyimino-3-methoxycyclohexa-2,5-dienylidene)-phenyl-acetonitrile 15.1 g (60 mmol) of crude (4-Hydroxyimino-3-methoxy-cyclohexa-2,5-dienylidene)-phenylacetonitrile are dissolved in 100 ml of anhydrous dimethylformamide (DMF) and cooled in an ice bath. After adding 5.1 ml (66 mmol) of methanesulfonyl chloride, 12.5 ml (90 mmol) of triethylamine are added dropwise to the solution, keeping the temperature below 10° C. The reaction mixture is stirred in the ice bath for 2 hrs, and Thin Layer Chromatography (TLC) analysis indicates the presence of a small amount of starting material. The reaction mixture is diluted in 250 ml of iced water, and the product, which precipitates in part, is extracted in ethylacetate. The organic phase is washed with 0.2 N hydrochloric acid, water, and saturated aqueous sodium chloride. The organic phase is dried over $MgSO_4$, the solvent is distilled off, and the residue is purified by flash chromatography on $SiO_2$, using $CH_2Cl_2$ as eluent. 8.0 g (40%) of (3-Methoxy-4-methylsulfonyloxyimino-cyclohexa-2,5-dienylidene)-phenyl-acetonitrile are obtained in the form of an orange solid darkening at 145° C. and melting at 165–169° C. (dec.).

Elemental analysis ($C_{16}H_{14}N_2O_4S$): calc.: C 58.17% H 4.27% N 8.48% found: C 58.55% H 4.37% N 8.28%

EXAMPLES 11–53

The compounds of examples 11 to 53 are obtained according to the method described in example 1.2, using the corresponding educts. The structures and physical data are listed in table 1.

TABLE 1

| Ex. | Structure | Purification | Description/melting point |
|---|---|---|---|
| 11 | 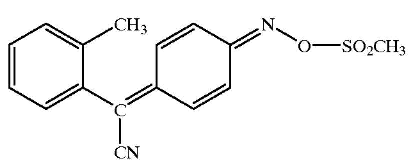 | recrystallization from toluene | yellow solid m.p. 50–58° C. |
| 12 | 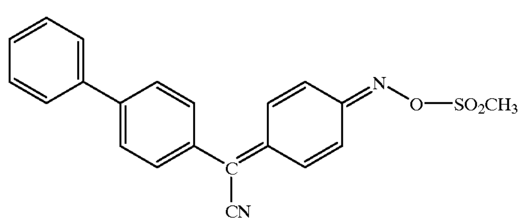 | recrystallization from toluene | brown solid m.p. 165–172° C. (dec) |
| 13 | 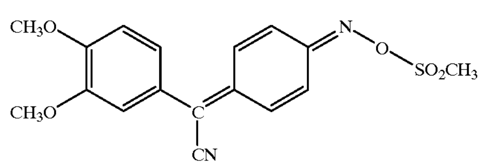 | recrystallization from toluene | orange solid m.p. 166–170° C. (dec) |
| 14 | 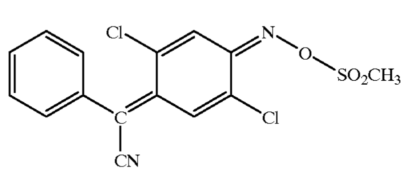 | chromatography (hexane:dichloromethane = 1:1) | yellow solid m.p. 159–161° C. (dec) |

TABLE 1-continued

| Ex. | Structure | Purification | Description/melting point |
|---|---|---|---|
| 15 | (3-methoxyphenyl)(cyano)methylene-cyclohexadienylidene N-O-SO$_2$CH$_3$ | recrystallization from toluene | yellow solid m.p. 120–122° C. (dec) |
| 16 | (4-chlorophenyl)(cyano)methylene-cyclohexadienylidene N-O-SO$_2$CH$_3$ | recrystallization from toluene | yellow solid m.p. 138–140° C. (dec) |
| 17 | (1-naphthyl)(cyano)methylene-cyclohexadienylidene N-O-SO$_2$CH$_3$ | recrystallization from methanol | yellow solid m.p. 149–155° C. (dec) |
| 18 | (2-methoxyphenyl)(cyano)methylene-cyclohexadienylidene N-O-SO$_2$CH$_3$ | chromatography (dichloromethane) | yellow solid m.p. 54–61° C. |
| 19 | (phenyl)(cyano)methylene-cyclohexadienylidene N-O-SO$_2$-(3-nitro-5-trifluoromethylphenyl) | recrystallization from toluene | yellow solid m.p. 186–188° C. (dec) |
| 20 | (phenyl)(cyano)methylene-cyclohexadienylidene N-O-SO$_2$-(pentafluorophenyl) | recrystallization from toluene | yellow solid m.p. 127–129° C. (dec) |
| 21 | (2-chlorophenyl)(cyano)methylene-cyclohexadienylidene N-O-SO$_2$CH$_3$ | recrystallization from mixture of ethyl acetate and hexane | beige solid m.p. 120–150° C. |
| 22 | (phenyl)(cyano)methylene-(2-phenyl)cyclohexadienylidene N-O-SO$_2$CH$_3$ | chromatography (hexane:dichloromethane = 3:7) | yellow solid m.p. 138–140° C. |

TABLE 1-continued

| Ex. | Structure | Purification | Description/ melting point |
|---|---|---|---|
| 23 | 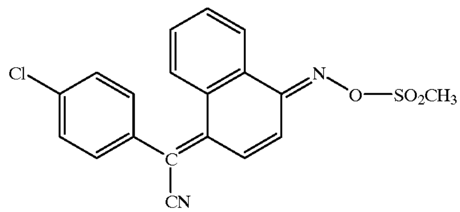 | recrystallization from mixture of toluene and 2-propanol | yellow solid m.p. 194–196° C. (dec) |
| 24 | 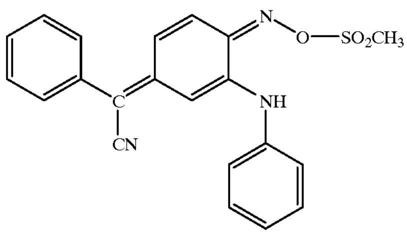 | chromatography (hexane:ethyl acetate = 7:3) | dark purple solid m.p. 136–140° C. (dec) |
| 25 | 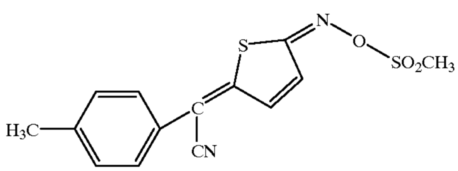 | recrystallization from toluene | yellow solid m.p. 148–150° C. (dec) |
| 26 | 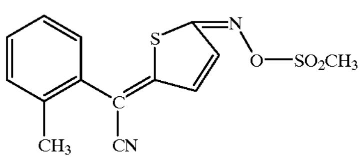 | recrystallization from 2-propanol | yellow solid m.p. 115–116° C. |
| 27 | 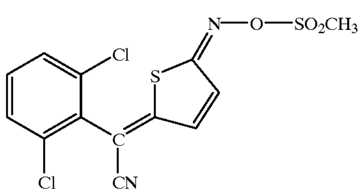 | recrystallization from 2-propanol | ochre solid m.p. 168–171° C. (dec) |
| 28 | 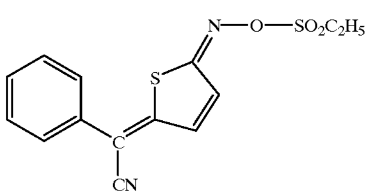 | recrystallization from 2-propanol | orange-brown solid m.p. 121–125° C. (dec) |
| 29 | 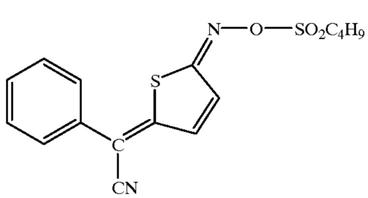 | recrystallization from 2-propanol | ochre solid m.p. 107–110° C. (dec) |

TABLE 1-continued

| Ex. | Structure | Purification | Description/ melting point |
|---|---|---|---|
| 30 | (2-chlorophenyl)(cyano)methylene thiophene N-O-SO₂CH₃ | recrystallization from 2-propanol | yellow solid m.p. 124–126° C. |
| 31 | phenyl(cyano)methylene thiophene N-O-SO₂-(3-CF₃-5-NO₂-phenyl) | recrystallization from toluene | yellow solid m.p. 171–172° C. (dec) |
| 32 | phenyl(cyano)methylene 3-C₄H₉-thiophene N-O-SO₂CH₃ | chromatography (dichloromethane) | ochre solid m.p. 64–69° C. |
| 33 | phenyl(cyano)methylene thiophene N-O-SO₂-(C₆F₅) | recrystallization from 2-propanol | brown solid m.p. 131–132° C. (dec) |
| 34 | (4-CH₃O₂SO-phenyl)(cyano)methylene thiophene N-O-SO₂CH₃ | recrystallization from mixture of 2-propanol and 1,2-dichloroethane | yellow-orange solid m.p. 172–175° C. (dec) |
| 35 | (2-methoxyphenyl)(cyano)methylene thiophene N-O-SO₂CH₃ | recrystallization from 2-propanol | ochre solid m.p. 145–148° C. (dec) |
| 36 | (2-methylphenyl)(cyano)methylene thiophene N-O-SO₂-(4-CH₃-phenyl) | recrystallization from 2-propanol | yellow solid m.p. 135–138° C. (dec) |

TABLE 1-continued

| Ex. | Structure | Purification | Description/melting point |
|---|---|---|---|
| 37 | (structure: 2-methylphenyl, thiophene, =N—O—SO$_2$C$_4$H$_9$, CN) | recrystallization from mixture of ethyl acetate and hexane | ochre solid m.p. 93–95° C. |
| 38 | (structure: 2-methylphenyl, thiophene, =N—O—SO$_2$C$_{16}$H$_{33}$, CN) | recrystallization from 2-propanol | yellow solid m.p. 107–108° C. |
| 39 | (structure: 2-methylphenyl, thiophene, =N—O—SO$_2$C$_8$H$_{17}$, CN) | recrystallization from 2-propanol | yellow-green solid m.p. 89–91° C. |
| 40 | (structure: 2-methylphenyl, thiophene, =N—O—SO$_2$—C$_6$H$_4$—OCH$_3$, CN) | recrystallization from 2-propanol | yellow solid m.p. 124–126° C. |
| 41 | (structure: phenyl, 2-methoxypyridine, =N—O—SO$_2$CH$_3$, CN) | recrystallization from mixture of ethanol and toluene | yellow solid m.p. 159–162° C. (dec) |
| 42 | (structure: phenyl, N-methylpyrrole, =N—O—SO$_2$CH$_3$, CN) | chromatography (hexane:ethyl acetate = 7:3) | yellow solid m.p. 156–160° C. |
| 43 | (structure: 2,4-dichlorophenyl, quinoid ring, =N—O—SO$_2$CH$_3$, CN) | recrystallization from toluene | brownish solid m.p. 159–166° C. (dec) |

TABLE 1-continued

| Ex. | Structure | Purification | Description/melting point |
|---|---|---|---|
| 44 | 2,4-dichlorophenyl-C(CN)=quinone-N-O-SO₂-CH(CH₃)₂ | chromatography (petroleum ether/ethyl acetate 3:1) | sticky resin |
| 45 | 2,4-dichlorophenyl-C(CN)=quinone-N-O-SO₂C₄H₉ | chromatography (petroleum ether/ethyl acetate 3:1) | viscous, brown oil |
| 46 | 2,4-dichlorophenyl-C(CN)=quinone-N-O-SO₂C₈H₁₇ | chromatography (petroleum ether/ethyl acetate 3:1) | brown, sticky solid (currently solidifying) |
| 47 | 2,4-dichlorophenyl-C(CN)=quinone-N-O-SO₂-C₆H₄-CH₃ | recrystallization from ethyl acetate | brownish solid m.p. 136–141° C. (dec) |
| 48 | 2,4-dichlorophenyl-C(CN)=quinone-N-O-SO₂-C₆H₄-C₁₂H₂₅ | chromatography (petroleum ether/ethyl acetate 9:1) | brown-redish oil |
| 49 | phenyl-C(CN)=quinone-N-O-SO₂-C₆H₄-C₁₂H₂₅ | chromatography (petroleum ether/ethyl acetate 9:1) | brown oil |
| 50[1] | phenyl-C(CN)=quinone-N-O-SO₂CH₃ | repetitive recrystallization from toluene | yellowish solid[1] m.p. 150–152° C. |

TABLE 1-continued

| Ex. | Structure | Purification | Description/ melting point |
|---|---|---|---|
| 51 | 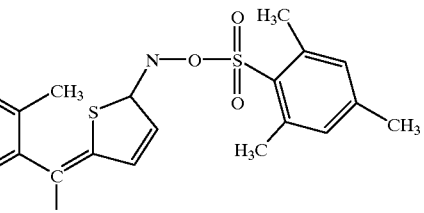 | recrystallization from 2-propanol | yellow solid m.p. 155–162° C. |
| 52 | 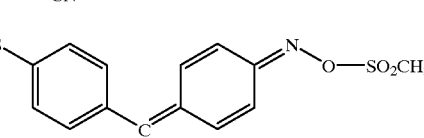 | recrystallization from 2-propanol | orange solid m.p. 158–163° C. |
| 53 | 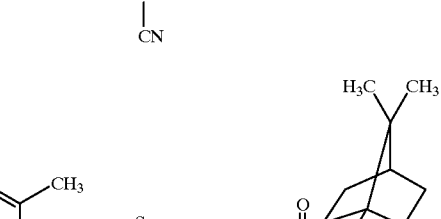 | recrystallization from 2-propanol | yellow-brown solid m.p. 134–136° C. |

[1]Same structure as example 1, but consisting of a pure stereoisomer ($^1$H-NMR; dxd of H—C (2 or 6) at 6.78 ppm. Tentatively assigned to the E-isomer. (dec) is decomposition.

EXAMPLE 54

Preparation of a Negative Resist

A resist solution is prepared by dissolving 65 parts of polyvinylphenol (Mw=4.000, Maruzen Chemicals Co. Ltd.), 30 parts of hexa(methoxymethyl)melamin (Cymell® 303, Cyanamid) and 5 parts of the latent acid to be tested in 7.5 g of 1-methoxy-2-propylacetat, which contains 1000 ppm of an anti-foaming agent (FC430). This solution is spin coated onto the polished side of a silicon wafer (diameter 4 inch), which has been pretreated with hexamethyldisilazan, by spinning at 5000 rpm for 30 seconds. The solvent is removed by drying the coated wafer for 60 seconds at 110° C. on a hot plate (pre-bake), which results in films of 1 μm thickness. Irradiation of the samples is performed with a Canon maskaligner (Canon PLA 501) using interference filters to select the wavelengths at 365, 405 and 436 nm. For each wavelength a fixed dose is used, but due to the lower output of the lamp and absorption of the latent acid, longer irradiation times respectively higher doses are used at longer wavelength in order to cause sufficient crosslinking. A special mask containing a greyscale step wedge (transmissions ranging from 0 to 50%) and resolution patterns are used. After exposure the wafers are heated for 60 seconds to 110° C. to perform the post exposure bake (PEB) during which the liberated acid catalyses the crosslinking reaction in the irradiated areas. Developing is performed by dipping the samples into a 2.38% solution of tetramethyl ammonium hydroxide (TMAH) for 60 seconds. The thickness of the film before exposure as well as after exposure in the fields that were exposed to different doses is measured with an Axiotron from Zeiss which uses white light interference. The thickness measurements are used to estimate the one-to-one energy E1:1 which is the dose that is required to retain the same film thickness as before developing. The film thickness of the cured samples is also measured by means of an Alpha Step profilometer. The step with the highest number that is cured is used to calculate the minimum dose E0 required to have crosslinking. The smaller more reactive is the latent acid.

The results are listed in Table 2 and show, that the latent acids have high sensitivity in a negative resist at all wavelengths.

TABLE 2

| Latent acid compound of example | Reactivity at 365 nm (mJ) | | Reactivity at 405 nm (mJ) | | Reactivity at 436 nm (mJ) | |
|---|---|---|---|---|---|---|
| 1 | E0 | 20 | E0 | 45 | E0 | 430 |
|  | E1:1 | 30 | E1:1 | 60 | E1:1 | 800 |
| 2 | E0 | 90 | E0 | 50 | E0 | 50 |
|  | E1:1 | 270 | E1:1 | 150 | E1:1 | 150 |
| 4 | E0 | 25 | E0 | 25 | E0 | 80 |
|  | E1:1 | 40 | E1:1 | 40 | E1:1 | 160 |
| 5 | E0 | 50 | E0 | 100 | E0 | 800 |
|  | E1:1 | 90 | E1:1 | 200 | E1:1 | >1000 |
| 6 | E0 | 35 | E0 | 30 | E0 | 60 |
|  | E1:1 | 70 | E1:1 | 60 | E1:1 | 120 |
| 7 | E0 | 70 | E0 | 45 | E0 | 35 |
|  | E1:1 | 210 | E1:1 | 90 | E1:1 | 70 |
| 8 | E0 | 30 | E0 | 9 | E0 | 9 |
|  | E1:1 | 50 | E1:1 | 15 | E1:1 | 15 |
| 9 | E0 | 25 | E0 | 35 | E0 | 350 |
|  | E1:1 | 40 | E1:1 | 70 | E1:1 | 700 |
| 10 | E0 | 50 | E0 | 50 | E0 | 70 |
|  | E1:1 | 100 | E1:1 | 100 | E1:1 | 140 |
| 11 | E0 | 25 | E0 | 100 | E0 | >1000 |

TABLE 2-continued

| Latent acid compound of example | Reactivity at 365 nm (mJ) | | Reactivity at 405 nm (mJ) | | Reactivity at 436 nm (mJ) | |
|---|---|---|---|---|---|---|
| | E1:1 | 50 | E1:1 | 200 | E1:1 | >1000 |
| 12 | E0 | 100 | E0 | 70 | E0 | 100 |
| | E1:1 | 200 | E1:1 | 140 | E1:1 | 250 |
| 14 | E0 | 30 | E0 | 30 | E0 | 250 |
| | E1:1 | 60 | E1:1 | 60 | E1:1 | 500 |
| 15 | E0 | 30 | E0 | 50 | E0 | 150 |
| | E1:1 | 60 | E1:1 | 100 | E1:1 | 300 |
| 16 | E0 | 50 | E0 | 55 | E0 | 500 |
| | E1:1 | 100 | E1:1 | 110 | E1:1 | 1000 |
| 17 | E0 | 70 | E0 | 100 | E0 | 140 |
| | E1:1 | 140 | E1:1 | 200 | E1:1 | 280 |
| 20 | E0 | 25 | E0 | 25 | E0 | 350 |
| | E1:1 | 50 | E1:1 | 50 | E1:1 | 700 |
| 21 | E0 | 30 | E0 | 300 | E0 | >1000 |
| | E1:1 | 60 | E1:1 | 600 | E1:1 | >1000 |
| 22 | E0 | 30 | E0 | 30 | E0 | 100 |
| | E1:1 | 60 | E1:1 | 60 | E1:1 | 200 |
| 23 | E0 | 600 | E0 | >1000 | E0 | >1000 |
| | E1:1 | >1000 | E1:1 | >1000 | E1:1 | >1000 |
| 25 | E0 | 20 | E0 | 10 | E0 | 8 |
| | E1:1 | 40 | E1:1 | 20 | E1:1 | 16 |
| 26 | E0 | 20 | E0 | 9 | E0 | 10 |
| | E1:1 | 40 | E1:1 | 20 | E1:1 | 18 |
| 27 | E0 | 22 | E0 | 11 | E0 | 15 |
| | E1:1 | 45 | E1:1 | 22 | E1:1 | 30 |
| 28 | E0 | 20 | E0 | 11 | E0 | 9 |
| | E1:1 | 40 | E1:1 | 22 | E1:1 | 18 |
| 29 | E0 | 30 | E0 | 11 | E0 | 11 |
| | E1:1 | 60 | E1:1 | 22 | E1:1 | 22 |
| 30 | E0 | 20 | E0 | 9 | E0 | 15 |
| | E1:1 | 40 | E1:1 | 18 | E1:1 | 30 |
| 33 | E0 | 20 | E0 | 10 | E0 | 20 |
| | E1:1 | 40 | E1:1 | 20 | E1:1 | 40 |
| 36 | E0 | 30 | not measured | | E0 | 13 |
| | E1:1 | 50 | | | E1:1 | 23 |
| 37 | E0 | 18 | not measured | | E0 | 9 |
| | E1:1 | 24 | | | E1:1 | 12 |
| 38 | E0 | 18 | not measured | | E0 | 11 |
| | E1:1 | 23 | | | E1:1 | 15 |
| 39 | E0 | 19 | not measured | | E0 | 5 |
| | E1:1 | 23 | | | E1:1 | 11 |
| 40 | E0 | 26 | not measured | | E0 | 10 |
| | E1:1 | 50 | | | E1:1 | 15 |
| 41 | E0 | 30 | E0 | 22 | E0 | 35 |
| | E1:1 | 60 | E1:1 | 44 | E1:1 | 70 |
| 50 | E0 | 13 | E0 | 37 | E0 | 230 |
| | E1:1 | 16 | E1:1 | 47 | E1:1 | 310 |

What is claimed is:

1. A compounds of the formulae I or II

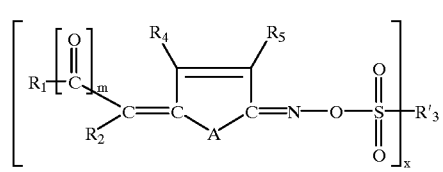 (I)

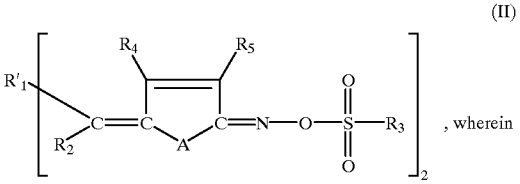 (II)

, wherein m is 0 or 1;
x is 1 or 2

$R_1$ is phenyl, which is unsubstituted or substituted by one or more of the radicals $C_1$–$C_{12}$alkyl, $C_1$–$C_4$haloalkyl, halogen, phenyl, $OR_6$, $NR_7R_8$, $SR_9$ or —S-phenyl, it being possible for the substituents $OR_6$, $SR_9$ and $NR_7R_8$ to form 5- or 6-membered rings, via the radicals $R_6$, $R_7$, $R_8$ or $R_9$, with further substituents on the phenyl ring or with one of the carbon atoms of the phenyl ring, or $R_1$ is naphthyl, anthracyl or phenanthryl, the radicals naphthyl, anthracyl and phenanthryl being unsubstituted or substituted by $C_1$–$C_6$alkyl, phenyl, $OR_6$, $NR_7R_8$, $SR_9$ or —S-phenyl, it being possible for the substituents $OR_6$, $SR_9$ and $NR_7R_8$ to form 5- or 6-membered rings, via the radicals $R_6$, $R_7$, $R_8$ or $R_9$ with further substituents on the naphthyl, anthracyl or phenanthryl ring or with one of the carbon atoms of the naphthyl, anthracyl or phenanthryl ring, or $R_1$ is a heteroaryl radical that is unsubstituted or substituted by $C_1$–$C_6$alkyl, phenyl, $OR_6$, $NR_7R_8$, $SR_9$ or —S-phenyl, it being possible for the substituents $OR_6$, $SR_9$ and $NR_7R_8$ to form 5- or 6-membered rings, via the radicals $R_6$, $R_7$, $R_8$ or $R_9$ with further substituents on the heteroaryl ring or with one of the carbon atoms of the heteroaryl ring, or, if m is 0, $R_1$ additionally is $C_2$–$C_6$alkoxycarbonyl, phenoxycarbonyl or CN; or $R_1$ is H or $C_1$–$C_{12}$alkyl, with the proviso that $R_2$ is not simultaneously H or alkyl;

$R'_1$ is $C_2$–$C_{12}$alkylene, phenylene, naphthylene,

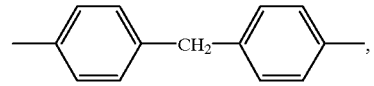

diphenylene or oxydiphenylene, the radicals phenylene, naphthylene,

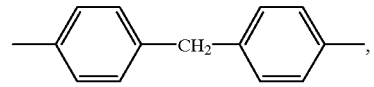

diphenylene and oxydiphenylene being unsubstituted or substituted by $C_1$–$C_{12}$alkyl;

$R_2$ has one of the meanings of $R_1$ or is unsubstituted or CN-substituted phenyl, $C_2$–$C_6$-alkanoyl, benzoyl that is unsubstituted or substituted by $C_1$–$C_6$alkyl, phenyl, $OR_6$, $SR_9$, $NR_7R_8$ or —S-phenyl, or $R_2$ is phenoxycarbonyl, $NO_2$, $C_1$–$C_4$haloalkyl, $S(O)_nC_1$–$C_6$alkyl, unsubstituted or $C_1$–$C_{12}$alkyl-substituted $S(O)n$—$C_6$–$C_{12}$aryl, $SO_2O$—$C_1$–$C_6$alkyl, $SO_2O$—$C_6$–$C_{10}$aryl, diphenyl-phosphinoyl or $NHCONH_2$, or $R_1$ and $R_2$ together with the CO group, form a 5- or 6-membered ring that is unsubstituted or substituted by $C_1$–$C_6$alkyl, phenyl, $OR_6$, $SR_9$, $NR_7R_8$ or —S-phenyl, and said ring may additionally be interrupted by O,S, $NR_7$ or by CO, and to which ring one or more benzo radicals may be fused;

n is 1 or 2; or $R_3$ is $C_1$–$C_{18}$alkyl, phenyl-$C_1$–$C_3$alkyl, camphoryl, $C_1$–$C_{10}$haloalkyl, phenyl, naphthyl, anthracyl or phenanthryl, the radicals phenyl, naphthyl, anthracyl and phenanthryl being unsubstituted or substituted by one or more of the radicals halogen, $C_1$–$C_4$haloalkyl, CN, $NO_2$, $C_1$–$C_{16}$alkyl, phenyl, $OR_6$, $COOR_9$, —OCO—$C_1$–$C_4$alkyl, $SO_2OR_9$ or $NR_7R_8$;

$R'_3$ when x is 1, has one of the meanings given for $R_3$, and when x is 2, $R'_3$ is $C_2$–$C_{12}$alkylene, phenylene, naphthylene,

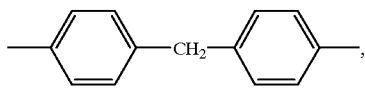

diphenylene or oxydiphenylene, the radicals phenylene, naphthylene,

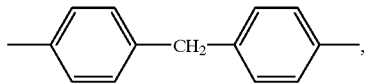

diphenylene and oxydiphenylene being unsubstituted or substituted by $C_1$–$C_{12}$alkyl;

$R_4$ and $R_5$ are independently of each other hydrogen, halogen, $C_1$–$C_6$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_6$, $SR_9$, $NR_7R_8$, $C_2$–$C_6$alkoxycarbonyl, phenoxycarbonyl, $S(O)_nC_1$–$C_6$alkyl, unsubstituted or $C_1$–$C_{12}$alkyl-substituted $S(O)_n$—$C_6$–$C_{12}$aryl, $SO_2O$—$C_1$–$C_6$alkyl, $SO_2O$—$C_6$–$C_{10}$aryl or $NHCONH_2$, or $R_4$ and $R_5$ together are —$C(R_{12})$=$C(R_{13})$—$C(R_{14})$=$C(R_{15})$—;

$R_6$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl or by $C_2$–$C_6$alkanoyl and said $C_1$–$C_{12}$alkyl may additionally be interrupted by —O—;

$R_7$ and $R_8$ are independently of each other hydrogen or $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl or $C_1$–$C_6$alkanoyl and said $C_1$–$C_{12}$alkyl may additionally be interrupted by —O—, or $R_7$ and $R_8$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_7$ and $R_8$, together with the nitrogen atom to which they are bonded, form a 5-, 6- or 7-membered ring which may be interrupted by —O— or by —$NR_6$—;

$R_9$ is $C_1$–$C_{12}$ alkyl which is unsubstituted or substituted by OH or $C_1$–$C_4$alkoxy and said $C_1$–$C_{12}$alkyl may additionally be interrupted by —O—;

A is S, O, $NR_6$, or a group of formula A1, A2, A3 or A4

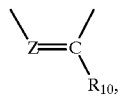
(A1)

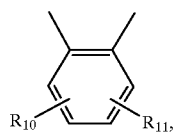
(A2)

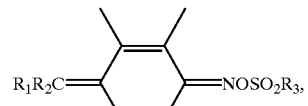
(A3)

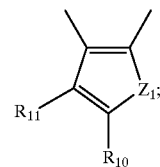
(A4)

$R_{10}$ and $R_{11}$ independently of each other have one of the meanings given for $R_4$, or $R_{10}$ and $R_{11}$ together are —CO—$NR_6$CO—, or $R_{10}$ and $R_{11}$ together are —$C(R_{12})$=$C(R_{13})$—$C(R_{14})$=$C(R_{15})$—;

$R_{12}$, $R_{13}$, $R_{14}$ and $R_{15}$ independently of one another are hydrogen, $C_1$–$C_4$alkyl, halogen, phenyl, $OR_6$, $SR_9$, $NR_7R_8$, —S-phenyl, $C_2$–$C_6$alkoxycarbonyl, phenoxycarbonyl, CN, $NO_2$, $C_1$–$C_4$haloalkyl, $S(O)_n$ $C_1$–$C_6$alkyl, unsubstituted or $C_1$–$C_{12}$alkyl-substituted $S(O)n$—$C_6$–$C_{12}$aryl, $SO_2O$—$C_1$–$C_6$alkyl, $SO_2O$—$C_6$–$C_{10}$aryl or $NHCONH_2$;

Z is $CR_{11}$ or N;

$Z_1$ is —$CH_2$—, S, O or $NR_6$.

2. A compound according to claim 1 of the formula I or II, wherein m is 0; x is 1; $R_1$ is unsubstituted phenyl or phenyl substituted by $C_1$–$C_6$alkyl, phenyl, $OR_6$, $SR_9$, —S-phenyl, halogen or $NR_7R_8$, it being possible for the substituents $OR_6$, and $NR_7R_8$ to form 5- or 6-membered rings, via the radicals $R_6$, $R_7$ or $R_8$, with further substituents of the phenyl ring or with one of the carbon atoms of the phenyl ring; $R'_1$ is phenylene, naphthylene,

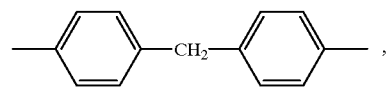

diphenylene or oxydiphenylene, the radicals phenylene, naphthylene,

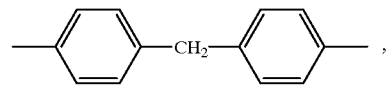

diphenylene and oxydiphenylene being unsubstituted or substituted by $C_1$–$C_{12}$alkyl.

3. Compounds according to claim 1, of the formula Ia

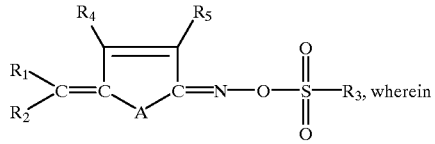
(Ia)

$R_1$, $R_2$, $R_3$, $R_4$, $R_5$ and A are as defined in claim 1.

4. Compounds according to claim 3, of formula Ia, wherein $R_1$ is unsubstituted phenyl or phenyl substituted once or twice by $C_1$–$C_4$alkyl, $OR_6$ or halogen or $R_1$ is naphthyl or thienyl;

$R_2$ is CN;

$R_3$ is $C_1$–$C_{16}$alkyl, camphoryl or unsubstituted phenyl or phenyl substituted by $C_1$–$C_{12}$alkyl, $C_1$–$C_4$alkoxy, $C_1$–$C_4$haloalkyl, $C_1$–$C_4$alkylthio, $NO_2$ or halogen;

$R_4$ and $R_5$ independently of each other are hydrogen, $C_1$–$C_4$alkyl, $C_1$–$C_4$alkoxy, $NR_7R_8$ or phenyl or $R_4$ and $R_5$ together are —C($R_{12}$)=C($R_{13}$)—C($R_{14}$)=C($R_{15}$)—;

$R_6$ is $C_1$–$C_4$alkyl or $C_1$14 $C_4$alkylsulfonyl;

$R_7$ and $R_8$ independently of one another are hydrogen or phenyl;

A is —S—, $NR_6$ or a group of the formula $A_1$

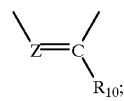

Z is $CR_{11}$ or N; and $R_{10}$, $R_{11}$, $R_{12}$, $R_{13}$, $R_{14}$ and $R_{15}$ are hydrogen.

5. A composition comprising
 a) at least one compound that can be crosslinked under the action of an acid and/or
 b) at least one compound the solubility of which is altered under the action of an acid and
 c) as latent acid photoinitiator, at least one compound of the formulae I or II according to claim 1.

6. A composition according to claim 5, which comprises in addition to component c) further photoinitiators, sensitisers or additives.

7. A method of crosslinking compounds that can be crosslinked under the action of an acid, which method comprises adding as a photosensitive acid a compound of formula I or II according to claim 1 to the above-mentioned compounds and irradiating imagewise or over the whole area with light having a wavelength of 180–1500 nm.

8. A photoresist based on oximesulfonates as photosensitive acid donors, the photoresist comprising as oximesulfonate a compound of formula I or II according to claim 1.

9. A photoresist according to claim 8, which photoresist is a negative resist.

10. A photoresist according to claim 8, which photoresist is a positive resist.

11. A photoresist according to claim 8, which photoresist is a chemically amplified resist.

12. A photoresist according to claim 8, comprising polymers that are transparent down to the wavelength region of 180 nm.

13. A method for the preparation of surface coatings, printing inks, printing plates, dental compositions, colour filters, resist materials and as image-recording material, or image-recording material for recording holographic images, which comprises irradiating a composition according to claim 5 with light having a wavelength of 180–1500 nm.

* * * * *